United States Patent
Lalonde et al.

(10) Patent No.: US 10,786,296 B2
(45) Date of Patent: Sep. 29, 2020

(54) SHAPE CHANGING ABLATION BALLOON

(71) Applicant: Medtronic CryoCath LP, Toronto (CA)

(72) Inventors: Jean-Pierre Lalonde, Candiac (CA); Scott W. Davie, Saint Paul, MN (US)

(73) Assignee: Medtronic CryoCath LP, Toronto, Ontario ( * ) Notice: Subject to any disclaimer, the term of this patent is extended or adjusted under 35 U.S.C. 154(b) by 505 days.

(21) Appl. No.: 15/812,081

(22) Filed: Nov. 14, 2017

(65) Prior Publication Data

US 2018/0071005 A1 Mar. 15, 2018

Related U.S. Application Data

(60) Division of application No. 14/255,625, filed on Apr. 17, 2014, now Pat. No. 9,855,089, which is a (Continued)

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00255* (2013.01); (Continued)

(58) Field of Classification Search
CPC ............ A61B 18/02; A61B 2018/0212; A61B 2018/0262; A61B 2018/0293; (Continued)

(56) References Cited

U.S. PATENT DOCUMENTS 3,833,004 A 9/1974 Vazquez et al.
4,315,512 A 2/1982 Fogarty
(Continued)

FOREIGN PATENT DOCUMENTS

CA 2666334 A1 3/2003
CA 2804690 A1 2/2012
(Continued)

OTHER PUBLICATIONS

Supplementary European Search Report, dated Oct. 12, 2017, for corresponding European Application No. EP 15 76 4746, consisting of 7 pages.
(Continued)

*Primary Examiner* — Thomas A Giuliani
(74) *Attorney, Agent, or Firm* — Christopher & Weisberg, P.A.

(57) ABSTRACT

A device, method, and system for thermally affecting tissue. The device may generally include an elongate body, an actuation element slidably disposed within the elongate body, a balloon defining an interior chamber, a proximal neck, and a distal neck, the first neck being coupled to the distal portion of the elongate body and the second neck being coupled to the distal portion of the actuation element, retraction of the actuation element within the elongate body causing the treatment element to transition from a first configuration to a second configuration. The distal neck may be located external to the interior chamber in the first configuration and within the interior chamber in the second configuration. The device may also include a fluid injection element that is transitionable to an expanded configuration when the balloon is inflated, thereby enhancing the cooling capacity of the balloon.

10 Claims, 15 Drawing Sheets

Related U.S. Application Data continuation-in-part of application No. 14/221,763, filed on Mar. 21, 2014, now Pat. No. 9,925,359.

(52) U.S. Cl.
CPC ............... *A61B 2018/00375* (2013.01); *A61B 2018/00577* (2013.01); *A61B 2018/0212* (2013.01); *A61B 2018/0262* (2013.01)

(58) Field of Classification Search
CPC .......... A61B 2018/00005; A61B 2018/00011; A61B 2018/00023; A61B 2018/0022; A61B 2018/00232; A61B 2018/00255; A61B 2018/00285; A61B 2018/00375
USPC ...................................................... 606/20–26
See application file for complete search history.

(56) References Cited

U.S. PATENT DOCUMENTS

| | | | |
|---|---|---|---|
| 5,108,370 | A | 4/1992 | Walinsky |
| 5,571,088 | A | 11/1996 | Lennox et al. |
| 5,766,151 | A | 6/1998 | Valley et al. |
| 5,868,735 | A | 2/1999 | Lafontaine |
| 5,997,503 | A | 12/1999 | Willis et al. |
| 6,053,913 | A | 4/2000 | Tu et al. |
| 6,117,101 | A | 9/2000 | Diederich et al. |
| 6,186,978 | B1 | 2/2001 | Samson et al. |
| 6,254,570 | B1 | 7/2001 | Rutner et al. |
| 6,432,080 | B2 | 8/2002 | Pederson, Jr. et al. |
| 6,468,268 | B1 | 10/2002 | Abboud et al. |
| 6,679,861 | B2 | 1/2004 | Yozu et al. |
| 6,942,640 | B2 | 9/2005 | Kokish |
| 7,708,716 | B2 | 5/2010 | Shah |
| 7,744,594 | B2 | 6/2010 | Yamazaki et al. |
| 7,780,628 | B1 | 8/2010 | Keren et al. |
| 8,460,240 | B2 | 6/2013 | Towler |
| 8,986,293 | B2 * | 3/2015 | Desrochers ....... A61M 25/0069 606/21 |
| 9,387,031 | B2 | 7/2016 | Stewart et al. |
| 2001/0016725 | A1 | 8/2001 | Valley et al. |
| 2002/0183731 | A1 | 12/2002 | Holland et al. |
| 2005/0015047 | A1 | 1/2005 | Shah |
| 2005/0203597 | A1 | 9/2005 | Yamazaki et al. |
| 2006/0259023 | A1 | 11/2006 | Abboud et al. |
| 2010/0241070 | A1 | 9/2010 | Blix et al. |
| 2012/0010485 | A1 | 1/2012 | Couronne et al. |
| 2012/0065633 | A1 | 3/2012 | Yagi et al. |
| 2012/0109116 | A1 * | 5/2012 | Asconeguy ............ A61B 18/02 606/21 |
| 2012/0302996 | A1 * | 11/2012 | Barash ............... A61M 25/0028 604/509 |
| 2013/0085493 | A1 | 4/2013 | Bloom et al. |
| 2013/0197499 | A1 * | 8/2013 | Lalonde ................. A61B 18/02 606/21 |

FOREIGN PATENT DOCUMENTS

| | | | |
|---|---|---|---|
| CA | 2862125 | A1 | 8/2013 |
| EP | 0203094 | A1 | 12/1986 |

OTHER PUBLICATIONS

International Search Report and Written Opinion dated Jun. 11, 2015, for corresponding International Application No. PCT/CA2015/000166; International Filing Date: Mar. 18, 2015 consisting of 8 pages.

Cook Medical, https://www.cookmedical.com/product/-/catalog/display?ds=uro_rpsbcs_webds, Mar. 21, 2014.

Olympus Australia, http://www.olympusaustralia.com.au/Product/Detail/719/B-V442Q-A-V-System-disposable-3-Lumen-Extraction-Balloon, Mar. 21, 2014.

Vention Medical, http://www.ventionmedical.com/, Mar. 21, 2014.

\* cited by examiner

SHAPE CHANGING ABLATION BALLOON

CROSS-REFERENCE TO RELATED APPLICATION

This application is a divisional of and claims priority to U.S. patent application Ser. No. 14/255,625, filed Apr. 17, 2014, now U.S. Pat. No. 9,855,089, entitled SHAPE CHANGING ABLATION BALLOON, which is a continuation-in-part of and claims priority to U.S. patent application Ser. No. 14/221,763, filed Mar. 21, 2014, now U.S. Pat. No. 9,925,359, entitled BALLOON DESIGN TO REDUCE DISTAL LENGTH, the entirety all of which is incorporated herein by reference.

STATEMENT REGARDING FEDERALLY SPONSORED RESEARCH OR DEVELOPMENT n/a

FIELD OF THE INVENTION

The present invention relates generally to catheters and methods for performing targeted tissue ablation in a subject. In particular, the present invention provides devices comprising catheters having balloons configured to reduce the distal length of the device while maintaining or improving cooling efficiency, and/or to reduce likelihood of delamination of the balloon from the catheter body.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. The ablation is often performed by passing energy, such as electrical energy, through one or more electrodes causing the tissue in contact with the electrodes to heats up to an ablative temperature, but may also be performed by freezing the tissue with the use of a cryoablation catheter.

Cryoablation catheters typically include an expandable element, such as a balloon, at the distal end. Although there are significant advantages of using balloons for cryoablation techniques, there are often associated disadvantages. First, to provide adequate attachment strength between a balloon and the catheter, the distal end of the balloon is often attached to a device distal tip, which may extend distally beyond the balloon. A balloon catheter with a distal tip can be difficult to position within the body, for example the right or left atrium of the heart. For a cryoablation technique to be effective, the distal end must be articulated with great accuracy to contact the balloon with the target tissue. Additionally, this technique is often performed in a very small space. A catheter with a long distal tip (one that extends past the distal neck of the balloon) or a balloon with extended distal and/or proximal necks can contribute to this steering difficulty.

Second, there is the concern that the balloon will burst from the application of pressurized cryofluid within, or the seal between the balloon and the body or shaft of the catheter will come undone (delamination). For the typically shaped catheter balloon, a balloon with a conical or ellipsoidal body and two necks, the outward pressure exerted on the balloon pushes the balloon material away from the catheter body or shaft. Longer necks with more attachment surface area are needed to securely attach the balloon to the catheter and prevent delamination due to the forces of pressure. This, in turn, creates longer balloons at the catheter distal tip that are more difficult to steer and precisely contact with target tissue.

When ablating around a pulmonary vein ostium, the success of the treatment may depend in part on whether there is adequate contact between the treatment element of the ablation device and the target tissue. Positioning the treatment element at the treatment site can be difficult, as the heart may be beating during the procedure. It may be beneficial to position at least a portion of the ablation device (for example, a portion of the treatment element) within the pulmonary vein in order to anchor the treatment element against the target tissue. However, although ablation of the pulmonary vein ostia may be an effective treatment for arrhythmia, ablation too far within the pulmonary vein, often referred to as being deep within the pulmonary vein, may cause adverse results, such as stenosis.

Another challenge presented by current ablation methods is the warming of the treatment element during cryoablation procedures. For example, a cryoballoon is cooled to a temperature sufficient to ablate tissue by the expansion and circulation of a coolant or cryogenic fluid within the cryoballoon. The effectiveness of the ablation procedure depends in part on the temperature of the ablation element, and it is therefore important that the treatment element, such as a cryoballoon, is maintained at ablation temperatures. However, the circulation of warm blood around the cryoballoon may increase the temperature of the cryoballoon, which may also increase the demand for coolant flow with the cryoballoon at increased flow rates, increased pressure, and/or increased cooling capacity of the system. Such demands may increase the risk of cryoballoon rupture and other system failures.

In light of the above, it is desirable to provide a cryoablation catheter with a shortened distal tip that not only is more easily manipulated within small spaces, but that also includes a balloon that is more resistant to delamination from the catheter body or shaft by making use of the balloon pressure to help reduce the tensile stress on the sealing or bonding agent. Currently used devices with balloons having everted necks experience the opposite effect, with the balloon pressure contributing to delamination. Additionally, glue joints are not particularly good at resisting tensile stress, unless in compression. It is further desirable to provide a method of using a cryoablation catheter with a shortened distal tip. It is a further desirable to provide a system and device that allows for accurate positioning of a treatment element against target tissue without causing ablation deep within the pulmonary vein, and that minimizes the warming effect of blood flow proximate the treatment element.

SUMMARY OF THE INVENTION

The present invention advantageously provides a device, system, and method for thermally affecting tissue and/or for minimizing tissue contact during an ablation procedure. The medical device may include an elongate body including a distal portion and a proximal portion, an actuation element slidably disposed within the elongate body, the actuation element including a distal portion and a proximal portion, an inflatable treatment element, such as a cryoballoon, defining an interior chamber, a first neck, and a second neck, the first neck being coupled to the distal portion of the elongate body and the second neck being coupled to the distal portion of the actuation element, retraction of the actuation element within the elongate body causing the treatment element to transition from a first configuration to a second configuration, each of the first and second necks being located external to the interior chamber in the first configuration and the second neck being located within the interior chamber in the second configuration. The second neck of the treatment element may include a first portion and a second portion, the first portion being coupled to the actuation element. For example, only the first portion of the second neck may be coupled, for example, bonded or mechanically coupled, to the actuation element. The distal portion of the actuation element may include a distal tip, the first portion being coupled led to the actuation element proximate the distal tip. Further, the second portion may separate from the actuation element when the treatment element is in the second configuration. For example, the first and second portions may each have an inner surface and an outer surface, the outer surface of the second portion being in contact with the outer surface of the first portion when the treatment element is in the second configuration. The treatment element may define a distal face when the treatment element is in the second configuration. Further, the treatment element may define a maximum outer diameter when the treatment element is in the second configuration, which may be located a distance from the distal face in a proximal direction. For example, the maximum diameter may be between approximately 3 mm and approximately 6 mm from the distal face in a proximal direction, or the maximum outer diameter may be located immediately proximal to the distal face. The distance between the maximum outer diameter and the distal face may change as the treatment element transitions between the first configuration and the second configuration. The device may further include a fluid injection element located within the interior chamber of the treatment element, at least a portion of the fluid injection element being in contact with the actuation element. The fluid injection element may have a first configuration in which the fluid injection element is substantially in contact with the actuation element and a second configuration in which at least a portion of the fluid injection element is expanded away from the actuation element. For example, the fluid injection element may be in the first configuration when the treatment element is in the first configuration and the fluid injection element may be in the second configuration when the treatment element is in the second configuration. Additionally, the fluid injection element may have a plurality of ports, at least some of the plurality of ports being proximate an inner wall of the treatment element when the treatment element is in the second configuration.

A method for performing a pulmonary vein isolation procedure may include positioning a medical device in a first configuration proximate a pulmonary vein ostium, the medical device including: an elongate body including a distal portion and a proximal portion; an actuation element slidably disposed within the elongate body, the actuation element including a distal portion and a proximal portion; an inflatable treatment element defining an interior chamber, a first neck, and a second neck, the first neck being coupled to the distal portion of the elongate body and the second neck being coupled to the distal portion of the actuation element, each of the first and second necks being located external to the interior chamber when the device is in the first configuration; and a fluid injection element located within the interior chamber, at least a portion of the fluid injection element being coiled around and substantially in contact with a portion of the actuation element; positioning the treatment element in contact with the pulmonary vein ostium, at least a portion of the second neck being located within the pulmonary vein; retracting the actuation element to transition the treatment element from the first configuration to a second configuration, the second neck being located within the interior chamber in the second configuration, retraction of the actuation element causing the fluid injection element to expand away from the actuation element; and circulating cryogenic fluid within the interior chamber. The method may further include initiating a flow of cryogenic fluid within the interior chamber before retracting the actuation element to transition the treatment element from the first configuration to a second configuration. Additionally or alternatively, the method may further include initiating a flow of cryogenic fluid within the interior chamber after retracting the actuation element to transition the treatment element from the first configuration to a second configuration. The treatment element may define a distal face when the treatment element is in the second configuration.

A method for minimizing tissue contact during an ablation procedure may include positioning a medical device having a cryoballoon in contact with a pulmonary vein ostium such that a distal neck of the cryoballoon is located external to a cryoballoon interior chamber and within the pulmonary vein and retracting an actuation element in mechanical communication with the cryoballoon to cause the distal neck to invert and become located within the cryoballoon interior chamber.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
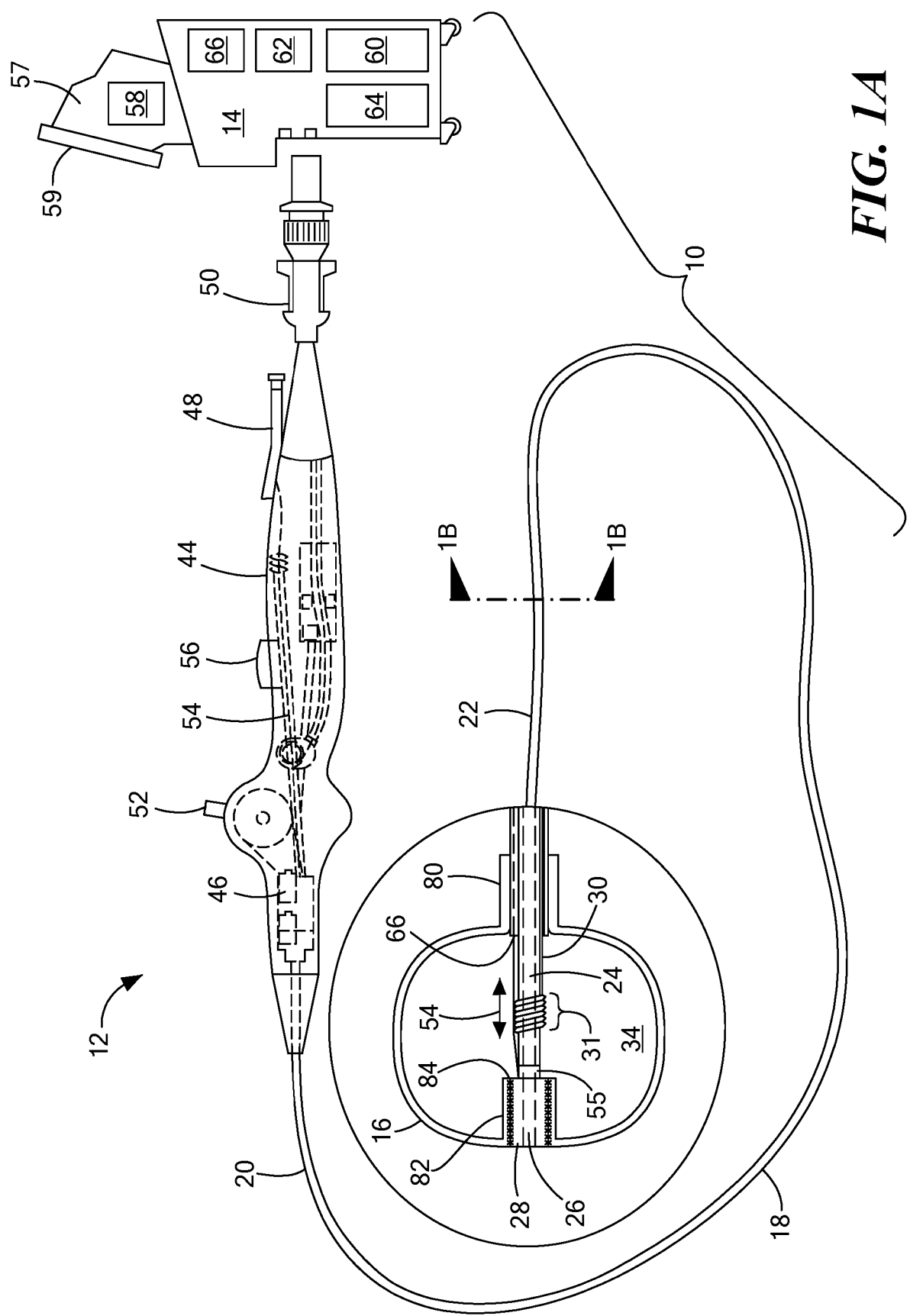
FIG. 1A shows a generalized medical system constructed in accordance with the principles of the present invention.

The present invention advantageously provides a medical system, specifically, a balloon catheter, that is more easily navigated within the body of a patient and that includes a balloon that is more resistant to bursting and delamination. Referring now to the drawing figures in which like reference designations refer to like elements, an embodiment of a medical system constructed in accordance with principles of the present invention is shown in FIG. 1A and generally designated as "10." The system 10 generally includes a medical device 12 that may be coupled to a control unit 14 or operating console. The medical device 12 may generally include one or more treatment regions, including at least one balloon 16, for energetic or other therapeutic interaction between the medical device 12 and a treatment site. The treatment region(s) may deliver, for example, cryogenic therapy, radiofrequency energy, or other energetic transfer with a tissue area in proximity to the treatment region(s), including cardiac tissue.

The medical device 12 may define a longitudinal axis 17 and include an elongate body 18 passable through a patient's vasculature and/or proximate to a tissue region for diagnosis or treatment, such as a catheter, sheath, or intravascular introducer. The elongate body 18 may define a proximal portion 20 and a distal portion 22, and may further include one or more lumens disposed within the elongate body 18 thereby providing mechanical, electrical, and/or fluid communication between the proximal portion of the elongate body 18 and the distal portion of the elongate body 18, as discussed in more detail below.

The medical device 12 may include a rigid or semi-rigid shaft or actuation element 24 at least partially disposed within a portion of the elongate body 18. The actuation element 24 may extend or otherwise protrude from a distal end of the elongate body 18, and may be movable with respect to the elongate body 18 in longitudinal and rotational directions. That is, the actuation element 24 may be slidably and/or rotatably moveable with respect to the elongate body 18. The actuation element 24 may further define a lumen 26 therein for the introduction and passage of a guide wire and a distal portion 25. The actuation element 24 may comprise a plurality of sections, each section having a varying diameter, with the shaft terminating in or otherwise including an area having a larger diameter than the rest of the actuation element 24, which may be referred to as a distal tip 28. The distal tip 28 may define an opening and passage therethrough that is in communication with the shaft lumen 26. As discussed in greater detail below, the balloon 16 may be attached to the distal tip 28. However, it will be understood that the actuation element 24 may have a single continuous diameter with the balloon 16 being attached to the shaft proximate the distal end of the shaft.

The medical device 12 may further include a fluid delivery conduit 30 traversing at least a portion of the elongate body 18 and towards the distal portion 22. The delivery conduit 30 may be coupled to or otherwise extend from the distal portion 22 of the elongate body 18 into the balloon 16. One or more fluid injection elements 31 in fluid communication with the fluid delivery conduit 30 may be disposed within the balloon 16. As a non-limiting example, a fluid injection element 31 may include a plurality of windings about the actuation element 24 (as shown in FIG. 10). At least a portion of the fluid injection element 31 may be configured to expand from the actuation element 24 toward the inner walls of the balloon 16 as the balloon 16 is expanded or inflated. Although not shown in FIGS. 1-9, the fluid injection element 31 may be expandable as shown and described in FIGS. 10-14. As a non-limiting example, the deployment of the fluid injection element 31 may be directly linked to the deployment of the balloon 16 or by a separate mechanism controlled by the console or by the operator via a button, lever, or the like. So, the fluid injection element 31 may be expanded automatically, semi-automatically, or manually independent of the inflation state of the balloon 16. The fluid delivery conduit 30 and/or fluid injection element 31 may be flexible, constructed from a shape memory material (such as Nitinol), and/or include other controllably deformable materials that allow the fluid delivery conduit 30 and/or fluid injection element 31 to be manipulated into a plurality of different geometric configurations, shapes, and/or dimensions. Alternatively, the delivery conduit 30 may be otherwise coupled to the actuation element 24 of the medical device 12, or may be disposed within the actuation element 24 with the shaft defining one or more openings through which fluid may pass into the balloon (for example, as shown in FIG. 4). Although a fluid delivery conduit is not expressly shown in FIGS. 5-9 for simplicity, it will be understood that the devices shown in all figures may have any suitable, fluid delivery conduit including those shown in FIGS. 1A, 4, and 10-14.

The fluid delivery conduit 30 may define a lumen therein for the passage or delivery of a fluid from the proximal portion of the elongate body 18 and/or the control unit 14 to the distal portion and/or treatment region of the medical device 12. The fluid delivery conduit 30 may further include one or more openings or ports 32 therein to provide for the dispersion or directed ejection of fluid from the lumen to the interior chamber 34 of the balloon 16.

The medical device 12 may further include a handle 44 coupled to the proximal portion 20 of the elongate body 18. The handle 44 can include circuitry for identification and/or use in controlling of the medical device 12 or another component of the system 10. For example, the handle 44 may include one or more pressure sensors 46 to monitor the fluid pressure within the medical device 12. Additionally or alternatively, the sensors 46 may be disposed within the balloon 16, on an outer surface of the balloon 16, on the actuation element 24 or elongate body 18, within one or more lumens, and/or anywhere else within the system that would provide desired data. Additionally, the handle 44 may be provided with a fitting 48 for receiving a guide wire that may be passed into the guide wire lumen 26. The handle 44 may also include connectors 50 that are matable directly to a fluid supply/exhaust and control unit 14 or indirectly by way of one or more umbilicals. The handle 44 may further include blood detection circuitry in fluid and/or optical communication with the injection, exhaust and/or interstitial lumens. The handle 44 may also include a pressure relief valve in fluid communication with the fluid delivery conduit 30 and/or exhaust lumen to automatically open under a predetermined threshold value in the event that value is exceeded.

The handle 44 may also include one or more actuation or control features that allow a user to control, deflect, steer, or otherwise manipulate a distal portion of the medical device from the proximal portion of the medical device. For example, the handle 44 may include one or more components such as a lever or knob 52 for manipulating the elongate body 18 and/or additional components of the medical device 12. For example, a pull wire with a proximal end and a distal end may have its distal end anchored to the elongate body 18 at or near the distal portion 22. A proximal end of the pull wire 54 may be anchored to an element such as a cam in communication with and responsive to the lever 52. A distal end of the pull wire 54 may be attached or coupled to a portion of elongate body 18 or the actuation element 24. As a non-limiting example, the pull wire 54 may be coupled to a coupling element 55 that is, in turn, coupled to the actuation element 24 (as shown in the figures). However, it will be understood that the pull wire 54 may be coupled to the device in any manner suitable to create at least one point of inflection (that is, a location at which the device may bend during navigation through the patient's vasculature) in a desired location on the elongate body 18 and/or the treatment element. The medical device 12 may include an knob, wheel, lever, or the like 56 that is movably coupled to the proximal portion of the elongate body 18 and/or the handle 44, and which may further be coupled to a proximal portion of the actuation element 24 such that manipulating the knob, wheel, lever, or the like 56 in a longitudinal direction causes the actuation element 24 to slide towards either of the proximal or distal portions of the elongate body 18. Moreover, all steering elements of the handle 44 may be movably coupled to the handle 44 such that each is movable into individual, distinct positions, and is able to be releasably secured in any one of the distinct positions. The handle 44 may also include one or more rotational actuation elements for rotating the actuation element 24 and/or a guide wire.

The control unit 14 may include one or more computers 57 that include one or more processors 58 for receiving signals from one or more sensors throughout the system 10, and or for the automatic, semi-automatic, and/or manual operation of the system. For example, the system 10 may include one or more computers 57 having one or more user input devices by which a user can program system parameters such as the inflation and deflation of a balloon, circulation of coolant through the fluid delivery and recovery conduits, and/or the operation of one or more electrodes or other thermal delivery elements. Additionally, the user may use the user input devices to override the automatic operation of the system 10 either programmed into or predetermined by the control unit 14. Still further, signals received by the one or more processors 58 may be used to automatically or semi-automatically control the configuration of the balloon 16 (for example, by extending or retracting the actuation element 24). The system 10 may further include one or more displays 59, such as computer screens or other visual elements in communication with the one or more processors 58 and/or user input devices.

The system 10 may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

In an exemplary system, a fluid supply 60 including a coolant, cryogenic refrigerant, or the like, an exhaust or scavenging system for recovering or venting expended fluid for re-use or disposal, as well as various control mechanisms for the medical system may be housed in the control unit 14. In addition to providing an exhaust function for the catheter fluid supply, the console may also include pumps, valves, controllers or the like to recover and/or re-circulate fluid delivered to the handle, the elongate body, and/or the fluid pathways of the medical device 12. A vacuum pump 62 in the control unit 14 may create a low-pressure environment in one or more conduits within the medical device 12 so that fluid is drawn into the conduit(s)/lumen(s) of the elongate body 18, away from the distal portion and towards the proximal portion of the elongate body 18. For example, the control unit 14 may include a fluid recovery reservoir 64 that is in fluid communication with a fluid recovery conduit 65 that is, in turn, in fluid communication with the balloon 16. The control unit 14 may include one or more controllers, processors, and/or software modules containing instructions or algorithms to provide for the automated operation and performance of the features, sequences, or procedures described herein.

While the medical device 12 may be in fluid communication with a cryogenic fluid source to cryogenically treat selected tissue, it is also contemplated that the medical device 12 may alternatively or additionally include one or more electrically conductive portions or electrodes thereon coupled to a radiofrequency generator or power source 66 as a treatment or diagnostic mechanism. If the catheter 12 includes thermoelectric cooling elements or electrodes capable of transmitting radiofrequency (RF), ultrasound, microwave, electroporation energy, or the like, the elongate body 18 may include a lumen in electrical communication with a power source 66.

Figure 1B:
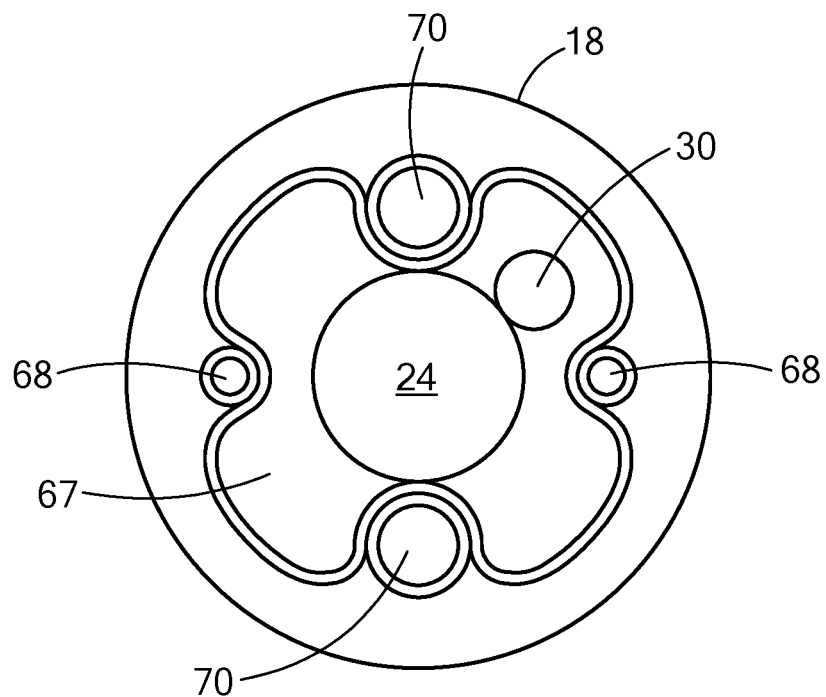
FIG. 1B shows a cross-sectional view of an exemplary elongate body of a medical device.

Referring now to FIG. 1B, a non-limiting, exemplary cross-sectional view of the elongate body 18 of the device is shown. The elongate body 18 may generally include an inner lumen 67, one or more pull wire lumens 68, and, optionally, one or more outer lumens 70. The inner lumen 67 may be sheathed by or defined by a layer of braided wire and/or a layer of Teflon (not shown for simplicity). The actuation element 24 and fluid delivery conduit 30 may be disposed within the inner lumen 67, and the space within the inner lumen 67 surrounding the actuation element 24 may be in communication with the vacuum 62 for the removal of expanded coolant from the distal end of the device. That is, the space within the inner lumen 67 surrounding the actuation element 24 may function as the fluid recovery conduit 65. One or more pull wires 54 may be located within the one or more pull wire lumens 68 on the outside of the inner lumen 67, although the pull wire 54 is shown in FIGS. 1A and 4-9 The one or more outer lumens 70 may serve as conduits for additional fluids, wires, sensors, or the like. However, it will be understood that other suitable configurations of interior components and lumens may also be used.

Referring now to FIGS. 1A through 9, at least one balloon 16 may be at the distal portion of the medical device 12. The at least one balloon 16 may be coupled to a portion of the elongate body 18 and also coupled to a portion of the actuation element 24 to contain a portion of the fluid delivery conduit 30 therein, as shown and discussed in more detail in FIGS. 2-9. Each balloon 16 may each define an interior chamber or region 34. For example, coolant or fluid dispersed from the fluid delivery conduit 30 may circulate within the interior chamber 34, and the interior chamber 34 may be in fluid communication with the fluid recovery conduit 65 defined by or included in the elongate body 18 for the removal of dispersed coolant from the interior chamber 34 of the balloon 16. In embodiments in which the device 12 includes more than one balloon, an additional fluid delivery conduit and/or fluid recovery conduit may fluidly connect the additional balloons to the control unit 14. The at least one balloon 16 may further include one or more material layers providing for puncture resistance, radiopacity, or the like.

Figure 2:
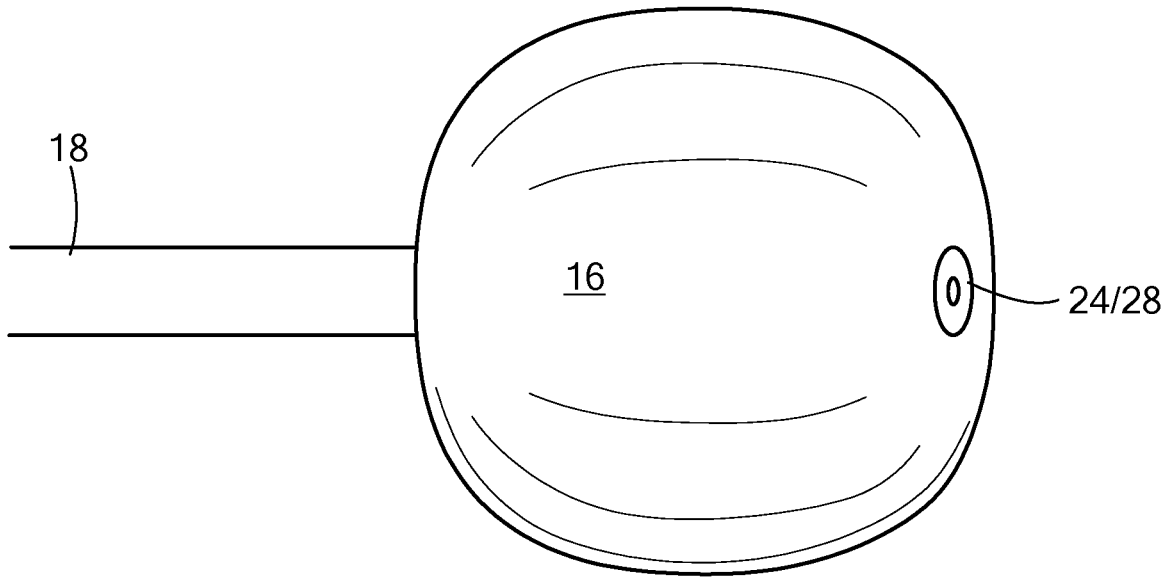
FIG. 2 shows a perspective view of a first embodiment of a medical device, in which both the proximal and distal necks are inverted.
Figure 3:
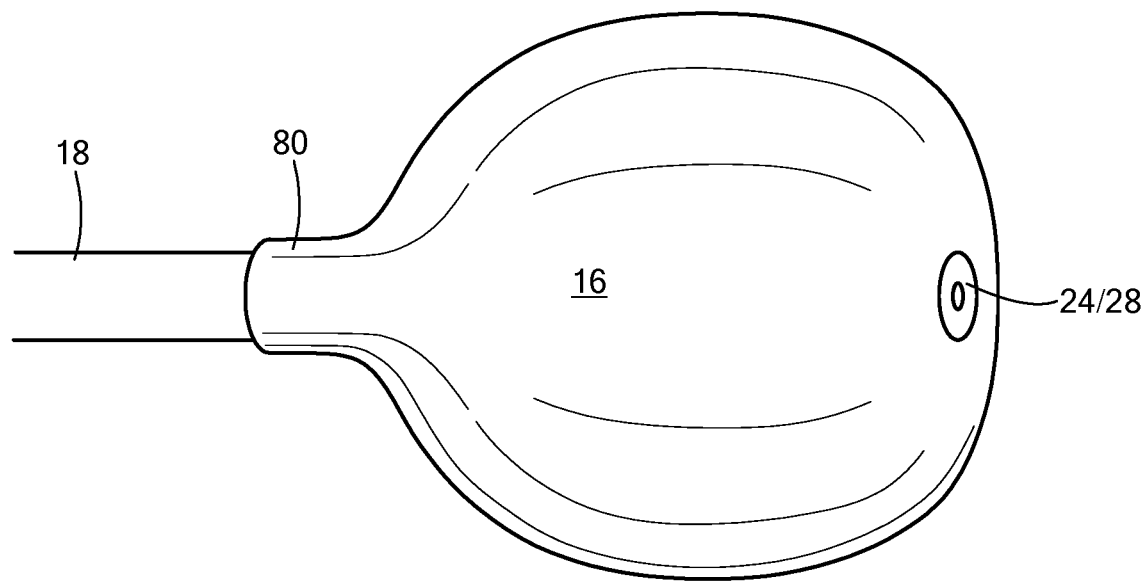
FIG. 3 shows a perspective view of a second embodiment of a medical device, in which the proximal neck is everted and the distal neck is inverted.
Figure 4:
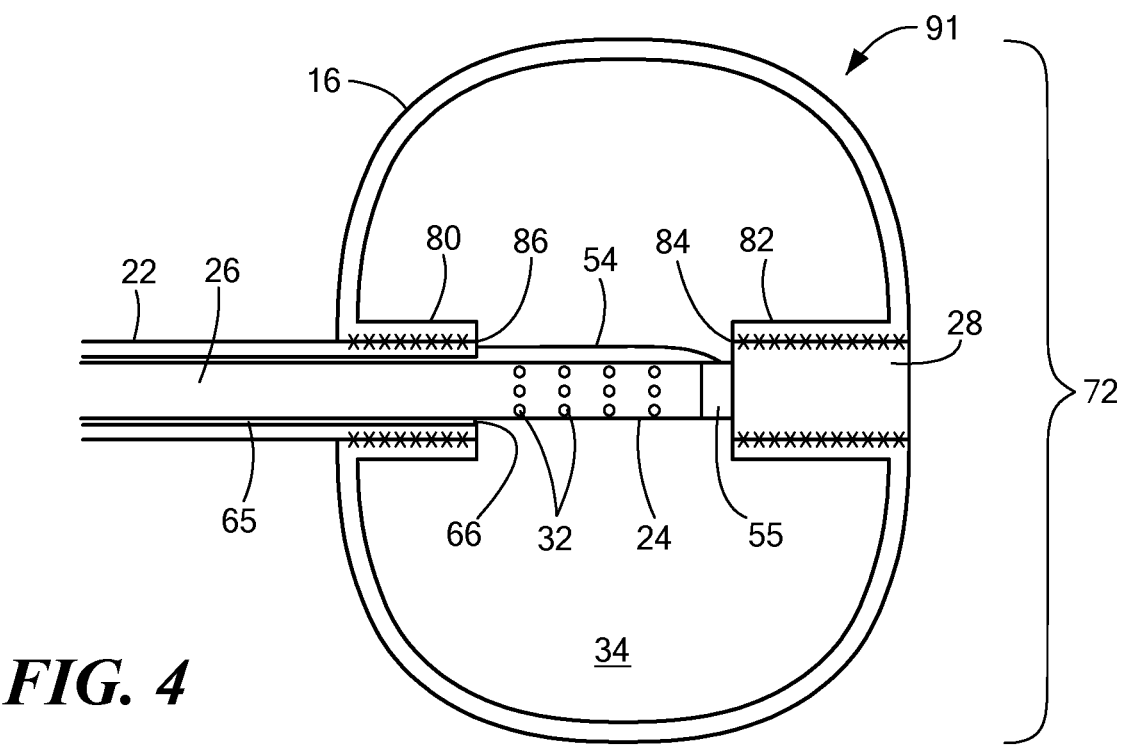
FIG. 4 shows a cross-sectional view of the first embodiment of the medical device of FIG. 2, in which the both the proximal and distal necks are inverted.

As shown in FIGS. 2-9, the distal end of the actuation element 24, for example, the distal tip 28, may be rounded to match the curvature of a balloon 16 when inflated, such that the balloon 16 may define a distal face 72 having a substantially continuous surface, without the actuation element 24 protruding beyond the balloon distal face 72. Further, the distal tip 28 or distal end of the actuation element 24 may be manufactured with a curved distal surface that matches a curve in the balloon distal face 72, enhancing the continuity between the actuation element 24 and the distal face 72. The shaft is depicted in FIGS. 2 and 3 as "24/28" to include embodiments in which the balloon 16 is generally coupled to the distal portion of the actuation element 24 and embodiments in which the balloon 16 is coupled to a distal tip 28 in particular. As a non-limiting embodiment, the distal face 72 may be slightly curved or arcuate, creating an atraumatic surface for safe navigation through the patient's vasculature and within the patient's heart. A substantially continuous arcuate surface without any projections may facilitate steering of the distal end of the medical device within the patient, especially in small spaces such as the chambers of the heart or vasculature. Although the balloon is shown in the figures as having a substantially spherical or rounded cubic shape, it will be understood that the balloon may have any suitable shape that allows for the inclusion of a shortened distal tip. The balloon may be manufactured such that at least a portion of each end of the balloon 16 forms an opening or neck 80, 82, which may have a narrower diameter than the balloon body 83 and/or may have a wall thickness that is different than that of the balloon body 83.

Figure 5:
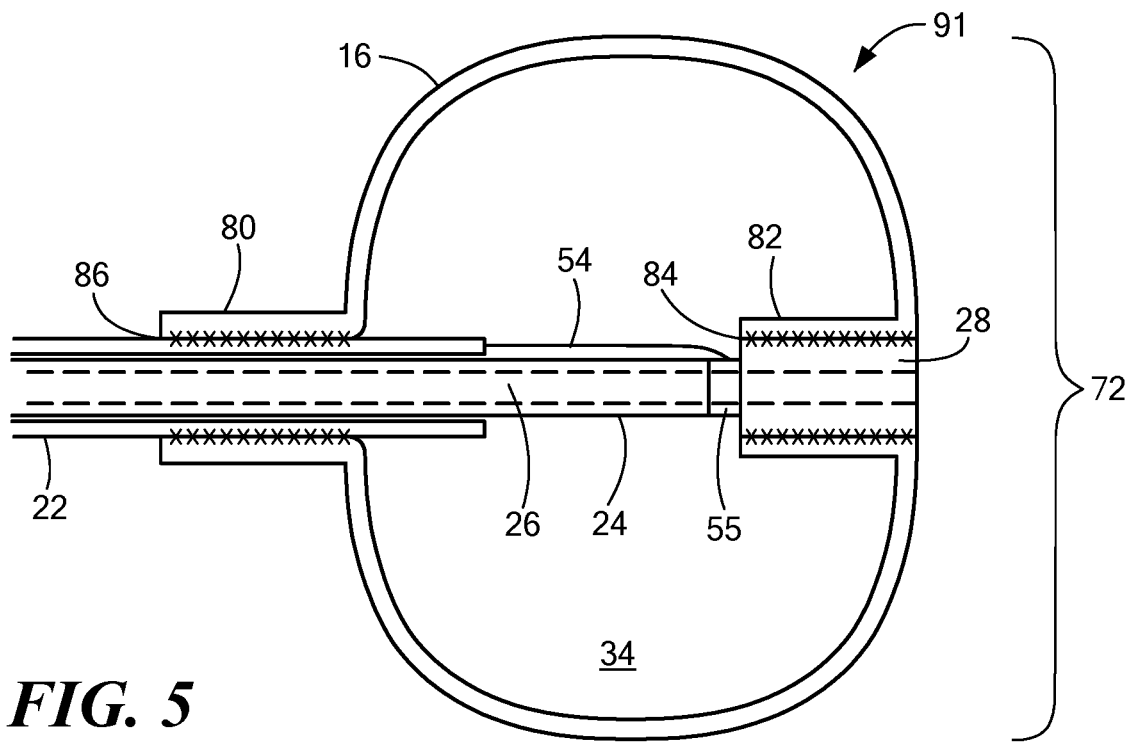
FIG. 5 shows a cross-sectional view of the second embodiment of the medical device of FIG. 3, in which the proximal neck is everted and the distal neck is inverted.

The medical device 12 may include a single balloon 16, as seen in FIGS. 4 and 5. The balloon 16 may have a proximal neck 80 at which the balloon 16 is coupled, by an adhesive junction or other joining means, to the distal portion 22 of the elongate body 18, and may further have a distal neck 82 at which the balloon 16 is coupled, by an adhesive junction or other joining means, to a distal portion of the actuation element 24, such as the distal tip 28. The distal neck 80 of the balloon 16 may be turned inward (in a distal-to-proximal direction) extending within the chamber 34 of the balloon 16. This may be referred to as the distal neck 80 being inverted. The inward extension of the distal neck 80 may form a distal seal 84 that is substantially coterminous with the actuation element 24, and may define a length of approximately 10% to 30% of the total length of the balloon 16 when the balloon is in an inflated state. The length of the inflated and uninflated balloon may be measured as a straightline distance between the proximalmost point and the distalmost point of the balloon 16. In the figures, all seals, which may also be referred to as "adhesive junctions," are stylistically depicted with hash marks for clarity.

As seen in FIG. 4, the expandable element may be substantially toroidal in shape, with the proximal neck 80 also being inverted (that is, turned inward, extending in a proximal-to-distal direction). In this configuration, an outer surface of the proximal neck 80 may be bonded, adhered, or otherwise in contact with and attached to an outer surface of the distal portion 22 of the elongate body 18 to create a proximal seal 86 extending within the balloon interior chamber 34. The proximal seal 86 may define a length of approximately 10% to 30% of the total length of the balloon 16 when in an inflated state. Alternatively, as seen in FIG. 5, the balloon 16 may include a proximal neck 80 that is everted (that is, turned outward, extending in a distal-to-proximal direction). In this configuration, an inner surface of the proximal neck 80 may be bonded, adhered, or otherwise in contact with and attached to an outer surface of the distal portion 22 of the elongate body 18 to create a proximal seal 86 extending without (that is, being external to) the balloon interior chamber 34 along an outer surface of the distal portion 22 of the elongate body 18. Further, the proximal neck 80 may be coupled to the distal portion 22 of the elongate body 18 such that the proximal neck 80 (proximate the balloon chamber 34) and the elongate body 18 are coterminous (for example, as shown in FIG. 4), or the proximal neck 80 may be coupled to the distal portion 22 of the elongate body 18 such that a portion of the elongate body 18 extends within the chamber 34 (for example, as shown in FIG. 5). In all embodiments, the balloon 16 may define a distal face 72 that has a substantially continuous surface that facilitates navigation of the device within the patient.

The medical device 12 may include more than one balloon. For example, FIGS. 6-9 show a medical device 12 having an inner balloon 88 and an outer balloon 90. The inner 88 and outer 90 balloons together may comprise the treatment element 91. The inner balloon 88 may contain a portion of the fluid delivery conduit 30 therein, and the outer balloon 90 may be disposed about the inner balloon 88. The inner 88 and outer 90 balloons in FIGS. 6-9 may be substantially similar to the single balloon 16 shown and described in the other figures, in composition, function, attachment, etc. The inner 88 and outer 90 balloons may be located substantially adjacent to or in contact with each other, and may define an interstitial space 92 between the balloons 88, 90 to facilitate detection and prevention of leaks from the first 88. For example, one or more sensors (such as impedance sensors, pressure sensors, and/or temperature sensors) may be located within the interstitial space to detect fluid leaks. In the embodiments shown in FIGS. 6 and 8, the interstitial space 92 may be very thin, even absent in some areas, especially when the inner balloon 88 is inflated and in contact with the outer balloon 90. In the embodiments shown in FIGS. 7 and 9, however, the interstitial space 92 may be larger in at least a portion of the treatment element. The two-balloon configuration may add strength to the treatment element, in that a delamination force resulting from inflation of the inner balloon 88 would have to overcome the seals of both the inner and outer balloons for the treatment element 91 to delaminate.

As shown in FIGS. 6-9, each of the inner 88 and outer 90 balloons may have a proximal neck 94, 96 coupled to an outer surface of the distal portion 22 of the elongate body 18, and a distal neck 98, 100 coupled to a portion of the actuation element 24, for example, the distal tip 28. In all of FIGS. 6-9, the outer balloon 90 may define a distal face 72 that has a substantially continuous surface that facilitates navigation of the device within the patient. For example, the actuation element 24 or distal tip 28 may be substantially coterminous with the distal balloon 90.

Continuing to refer to FIGS. 6-9, the inner balloon 88 may be substantially toroidal in shape, with the proximal neck 94 being inverted (that is, turned inward, in a proximal-to-distal direction) to form a first proximal seal 102 between an outer surface of the proximal neck 94 and an outer surface of the distal portion 22 of the elongate body 18, and the distal neck 98 being inverted (that is, turned inward, in a distal-to-proximal direction) to form a first distal seal 104 between an outer surface of the distal neck 98 and a distal portion of the actuation element 24 (for example, the distal tip 28), each seal 102, 104 extending within the interior chamber 34 of the inner balloon 88. Although the seals 102, 104 could also be described as extended within the interior chamber of the second balloon 90, the description is limited to extension within the interior chamber 34 of the inner balloon 88 for simplicity of reference. As is discussed in more detail below, the first proximal seal 102 and the first distal seal 104 of the inner balloon 88 may be attached to the elongate body 18 and actuation element 24, respectively. A second portion of each neck 94, 98 may be in contact with or substantially in contact with, but not attached to, a portion of the proximal and distal necks of the outer balloon 90. As such, fluid leaking from the inner balloon 88 may more easily flow between the inner 88 and outer 90 balloons for detection by a leak-detection sensor disposed in the interstitial space 92, such as a pressure or impedance sensor. The distal neck 98 and proximal neck 94 of the inner balloon 88 may each define a length of approximately 10% to 30% of the total length of the inner balloon 88 when the inner balloon 88 is in an inflated state, with the length of each neck 94, 98 being measured as a straightline distance between the proximalmost point and the distalmost point of the inner balloon 88.

The distal neck 100 of the outer balloon 90 may also be inverted (that is, turned inward, in a distal-to-proximal direction), extending within the interior chamber 34 of the inner balloon 88. An outer surface of the distal neck 100 of the outer balloon 90 may be bonded, adhered, or otherwise in contact with and attached to an outer surface of a distal portion of the actuation element 24 (for example, the distal tip 28) to create a distal seal 110 extending within the interior chamber 34 of the inner balloon 88. An inner surface of distal neck 100 of the outer balloon 90 may also be in contact with or substantially in contact with, but not attached to, an outer surface of the distal neck 98 of the inner balloon 88. At least a portion of the distal neck 98 of the inner balloon 88 may overlap the inverted distal neck 100 of the outer balloon 90.

Figure 6:
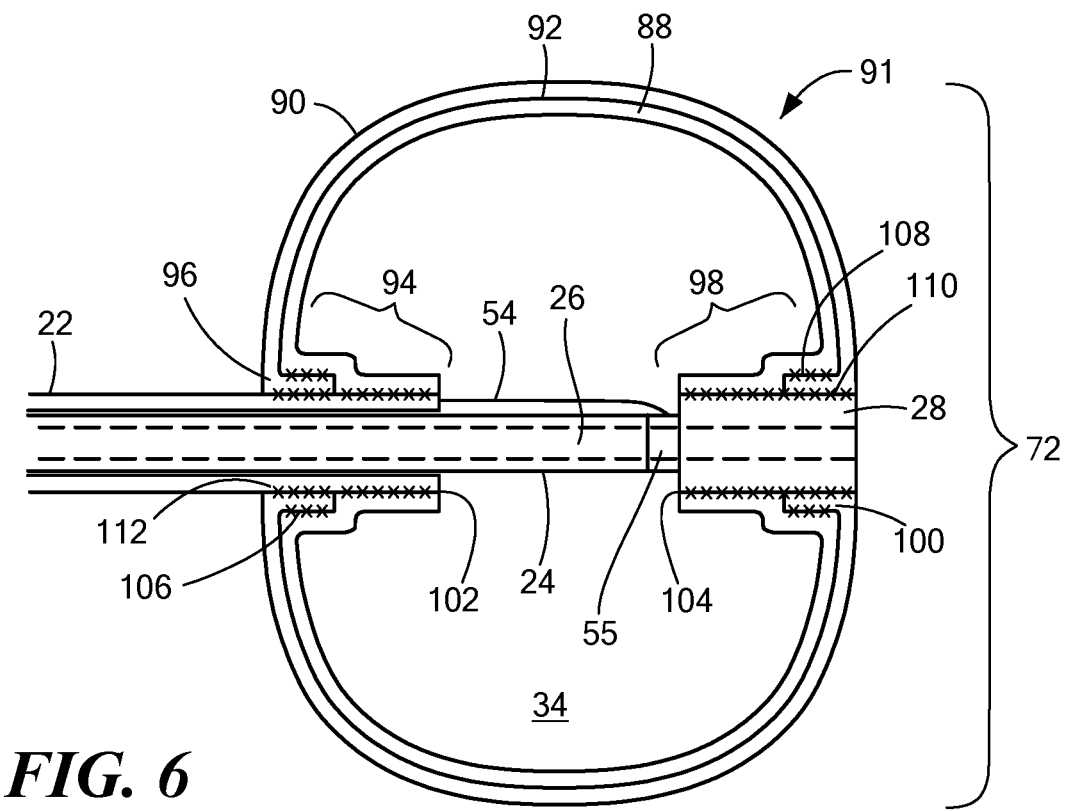
FIG. 6 shows a cross-sectional view of a third embodiment of a medical device, the device having two balloons with a first balloon symmetrically positioned within a second balloon and the proximal and distal necks of both balloons being inverted.
Figure 7:
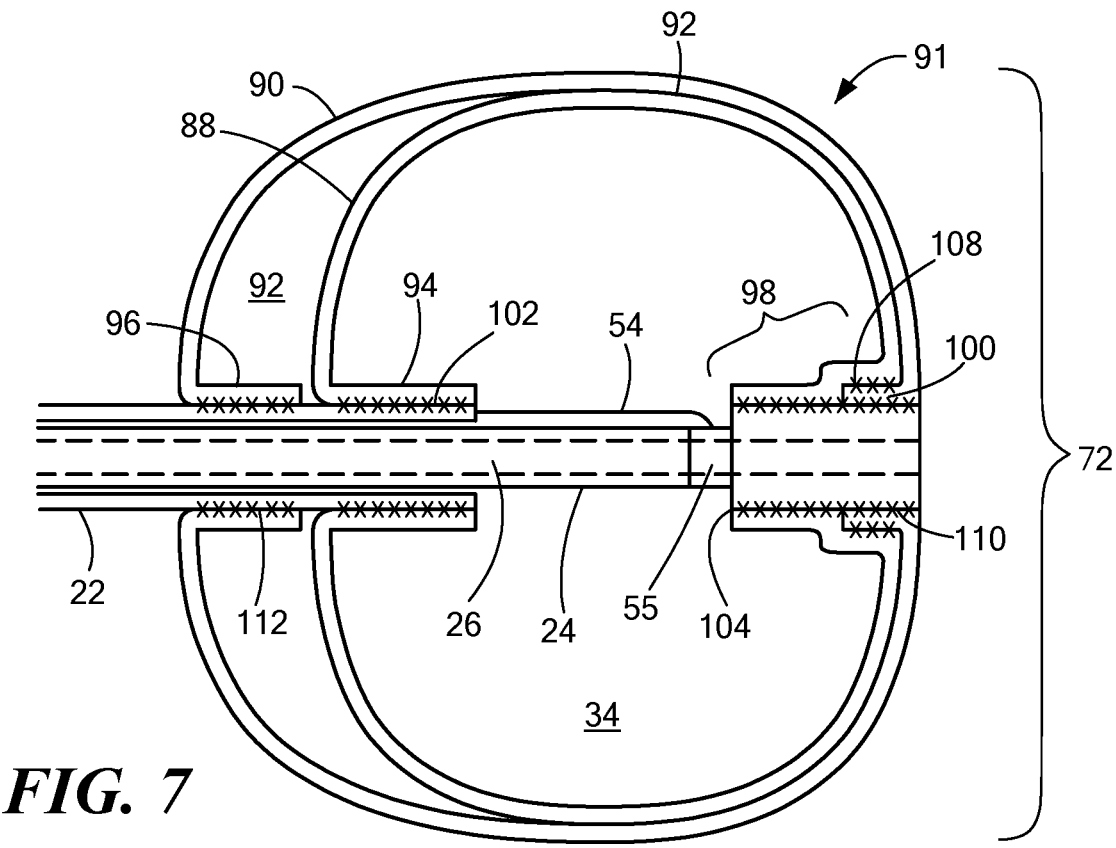
FIG. 7 shows a cross-sectional view of a fourth embodiment of a medical device, the device having two balloons with a first balloon asymmetrically positioned within a second balloon and the proximal and distal necks of both balloons being inverted.

Now referring in particular to FIGS. 6 and 7, the proximal neck 96 of the outer balloon 90 may also be inverted (that is, turned inward, in a proximal-to-distal direction), extending within the interior chamber 34 of the inner balloon 88. An outer surface of the outer balloon proximal neck 96 may be bonded, adhered, or otherwise in contact with and attached to an outer surface to the distal portion 22 of the elongate body 18 to form a proximal seal 112. The inner balloon 88 may be symmetrically or asymmetrically positioned within the outer balloon 90, depending on, for example, the desired maneuverability of the device, the procedure for which the device is used, and/or the desired cooling effect of the treatment element. For example, the device shown in FIG. 6 may have a more distal deflection point than the device shown in FIG. 7, because the layered proximal necks 94, 96 of the inner 88 and outer 90 balloons may increase the stiffness and decrease the flexibility of the device at or near the location at which the proximal necks 94, 96 are attached to the elongate body 18. This more distal deflection point may allow the device to be navigated through tortuous vasculature more easily. Additionally, the asymmetrical configuration shown in FIG. 7 may affect the cooling capacity of the treatment element 91. The larger interstitial space 92 between the inner 88 and outer 90 balloons may provide thermal insulation of the inner balloon 88, particularly the proximal portion of the inner balloon 88, from the warming effect of the surrounding blood. This, in turn, may enhance the cooling effect of, at least, the distal portion of the treatment element through the outer balloon 90. That is, the limited heat transfer from tissue and/or blood to the proximal portion of the inner balloon 88 may preserve and potentially concentrated the cooling capacity within the distal portion of the treatment element 91. The symmetrical configuration shown in FIG. 6 may allow cooling of both the proximal and distal portions of the treatment element 91. In a non-limiting embodiment, this symmetrical configuration may be useful when the device is inserted into the left atrium through a pulmonary vein, and then retracted so that the proximal portion of the treatment element 91 is in contact with the pulmonary vein ostium. In that case, the proximal portion, rather than the distal portion, of the treatment element 91 may be used to thermally treat the pulmonary vein ostium.

FIG. 6 shows a configuration in which the inner balloon 88 is symmetrically positioned within, and concentric with, the outer balloon 90. Both the inner 88 and outer 90 balloons in FIG. 6 may be toroidal in shape, with the proximal necks 94, 96 and distal necks 98, 100 of the balloons being inverted and extending within the interior chamber 34 of the inner balloon 88. In such an embodiment, an inner surface of the proximal neck 96 of the outer balloon 90 may be in contact with or substantially in contact with, but not attached to, an outer surface of the proximal neck 94 of the inner balloon 88. At least a portion of the proximal neck 94 of the inner balloon 88 may overlap the proximal neck 96 of the outer balloon 90. In this manner, a double-layered adhesive junction may be formed, which may further prevent delamination or tearing from occurring when the balloons are inflated and burst pressure is exerted.

FIG. 7 shows a configuration in which the inner balloon 88 may be asymmetrically positioned within the outer balloon 90. Both the inner 88 and outer 90 balloons may be toroidal in shape, but may not be concentric, unlike the configuration shown in FIG. 6. In the configuration shown in FIG. 7, the proximal neck 96 of the outer balloon 90 may be bonded, adhered, or otherwise in contact with and attached only to the distal portion 22 of the elongate body 18, without being overlapped by and coupled to at least a portion of the proximal neck 94 of the inner balloon 88. Further, the proximal neck 96 of the outer balloon 90 may not extend within the interior chamber 34 of the inner balloon 88, but may instead extend within the interstitial space 92 between the inner 88 and outer 90 balloons. Defined another way, the proximal neck 96 of the outer balloon 90 may be inverted within the treatment element 91 as a whole. As shown in FIG. 7, the portion of interstitial space 92 proximate the proximal necks 94, 96 of the inner 88 and outer 90 balloons may be larger than the portion of interstitial space 92 proximate the distal necks 98, 100 of the inner 88 and outer 90 balloons. This size of the interstitial space 92 proximal the proximal necks 94, 96 may be determined by the distance between the proximal seal 102 of the inner balloon 88 and the proximal seal 112 of the outer balloon 90.

Figure 8:
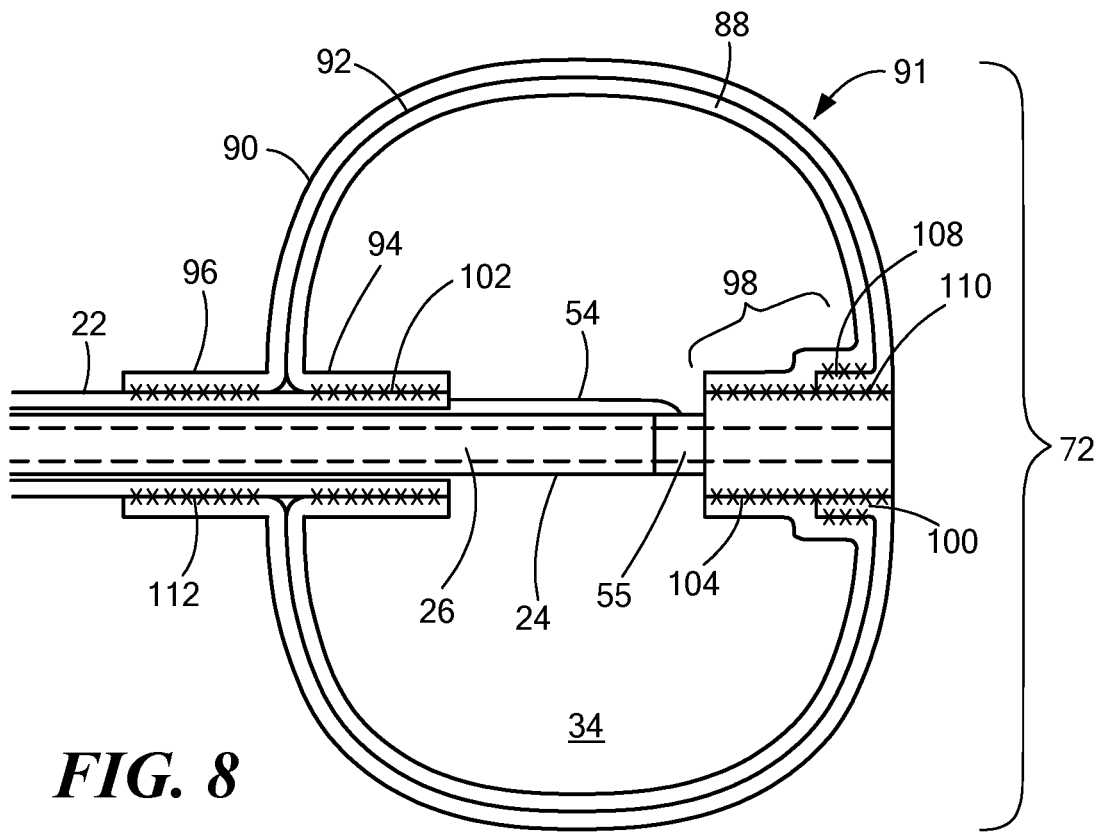
FIG. 8 shows an illustration of a cross-sectional view of a fifth embodiment of a medical device, the device having two balloons with a first balloon symmetrically positioned within a second balloon and the distal necks of both balloons being inverted, the proximal neck of the first balloon being inverted, and the proximal neck of the second balloon being everted.
Figure 9:
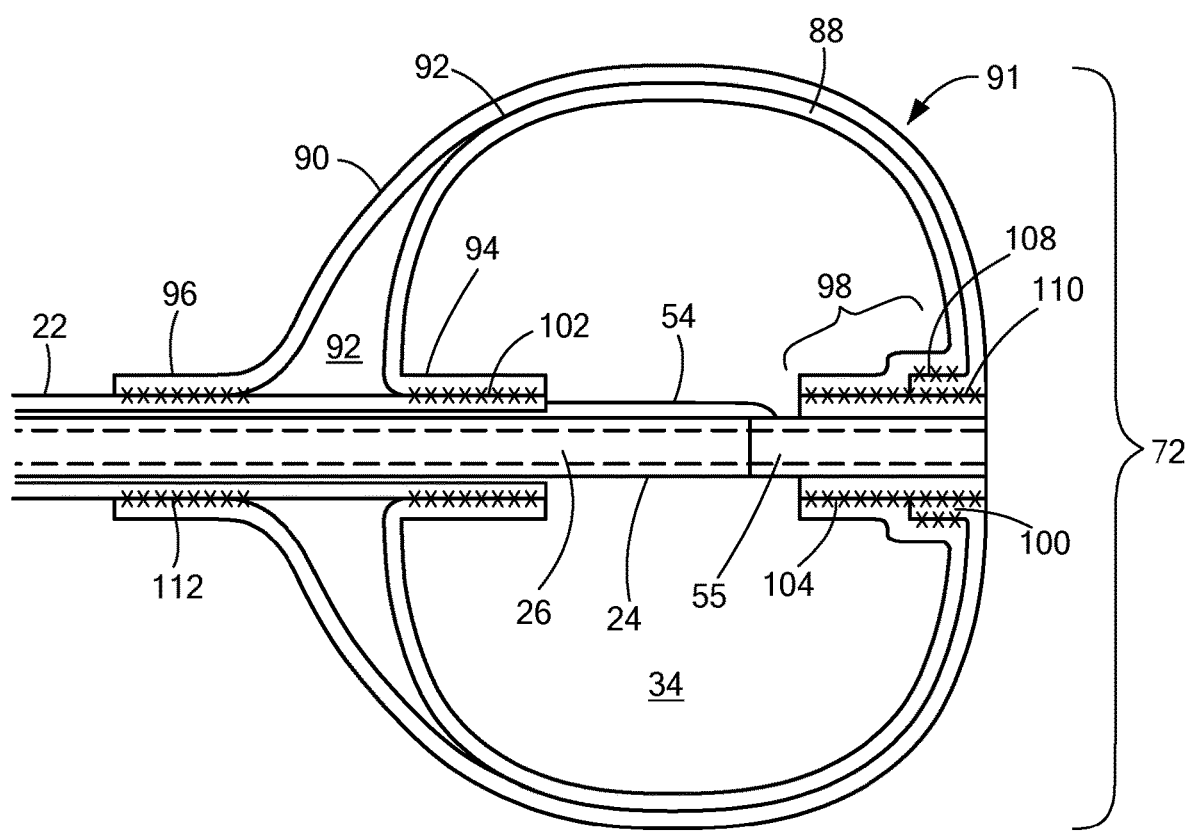
FIG. 9 shows a cross-sectional view of a sixth embodiment of a medical device, the device having two balloons with a first balloon asymmetrically positioned within a second balloon and the distal necks of both balloons being inverted, the proximal neck of the first balloon being inverted, and the proximal neck of the second balloon being everted.
Figure 10:
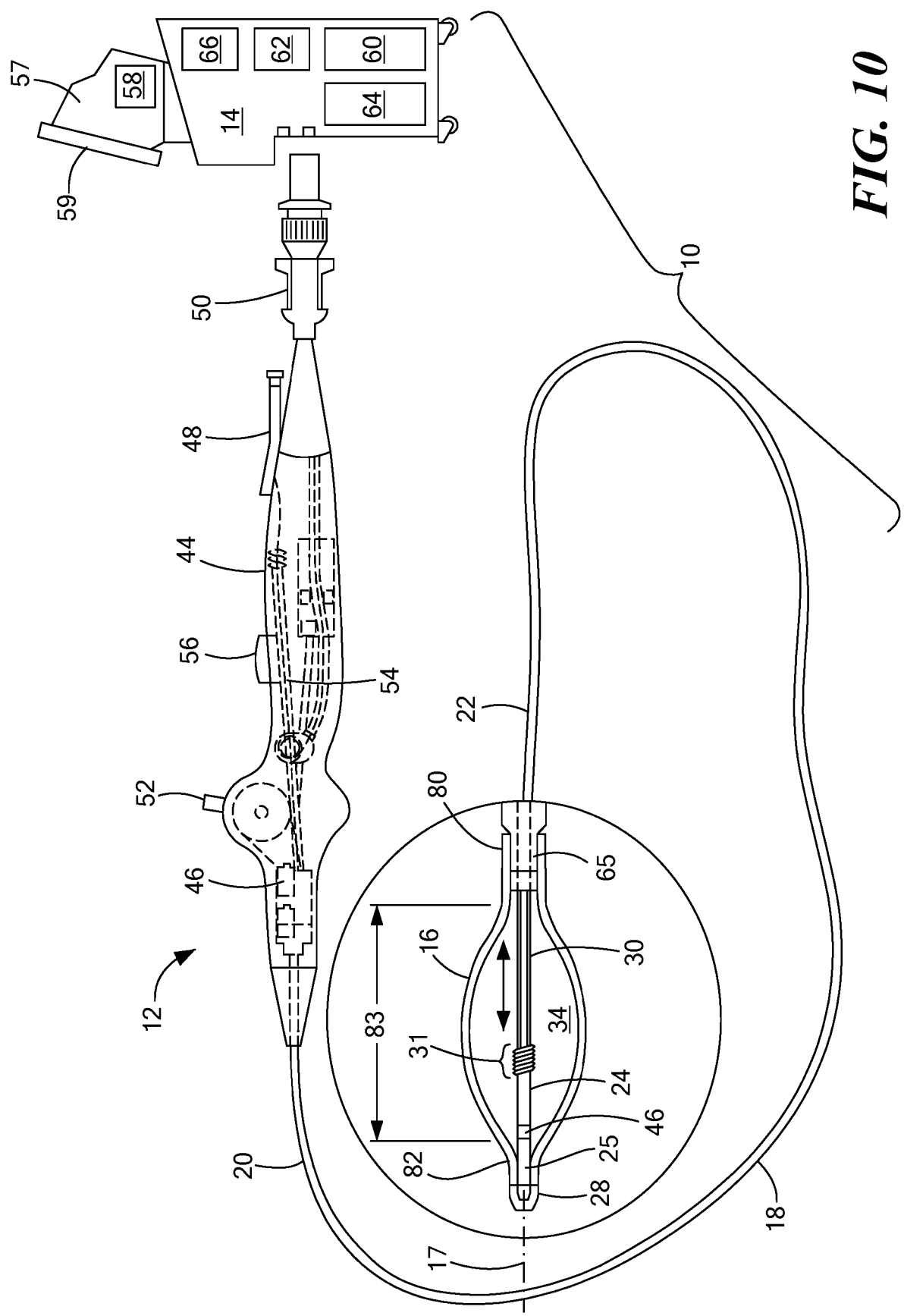
FIG. 10 shows a medical system including a medical device having a shape changing balloon, the balloon being in a first configuration.

Referring now to FIGS. 8 and 9, the proximal neck 96 of the outer balloon 90 may be everted (that is, turned outward, in a distal-to-proximal direction), extending without or being external to both the interior chamber 34 of the inner balloon 88 and the interstitial space 92 between the inner 88 and outer balloons 90. Defined another way, the proximal neck 96 of the outer balloon 90 may be everted on the outside of the treatment element 91 as a whole. An inner surface of the proximal neck 96 of the outer balloon 90 may be bonded, adhered, or otherwise in contact with and attached to the distal portion 22 of the elongate body 18 to form a first proximal seal 112. The inner balloon 88 may be symmetrically or asymmetrically positioned within the outer balloon 90, with the advantages of each configuration being as discussed above regarding FIGS. 6 and 7.

FIG. 8 shows a configuration in which the inner balloon 88 is symmetrically positioned within, and concentric with, the outer balloon 90. In such an embodiment, the proximal neck 96 of the outer balloon 90 may not be coupled to the proximal neck 94 of the inner balloon 88, but the proximal seal 112 of the outer balloon 90 and the proximal seal 102 of the inner balloon 88 may be substantially adjacent to each other, extending in opposite directions. For example, as shown in FIG. 8, the proximal seal 112 of the outer balloon 90 may extend be everted (that is, external to the treatment element 91) in a distal-to-proximal direction, and the proximal seal 102 of the inner balloon 88 may be inverted and extend within the interior chamber 88 (and the treatment element 91 as a whole) in a proximal-to-distal direction. The interstitial space 92 defined between the inner 88 and outer 90 balloons may only be wide enough to facilitate leak detection or leak containment within the outer balloon 90.

FIG. 9 shows a configuration in which the inner balloon 88 is asymmetrically positioned within the outer balloon 90. In such an embodiment, the proximal neck 96 of the outer balloon 90 may be coupled only to an outer surface of the distal portion 22 of the elongate body 18, without being coupled to the proximal neck 94 of the inner balloon 88. As shown in FIG. 9, the portion of interstitial space 92 proximal the proximal necks 94, 96 of the inner 88 and outer 90 balloons may be larger than the portion of interstitial space 92 proximate the distal necks 98, 100 of the inner 88 and outer 90 balloons. The size of the interstitial space 92 between the proximal necks 94, 96 may be determined by the distance between the proximal seal 102 of the inner balloon 88 and the proximal seal 112 of the outer balloon 90.

The continuously arcuate configuration of the distal portion of the medical device generally provides the ability to deliver therapeutic treatment more precisely, because of the absence of a protruding distal tip enhances ease of navigating the device. Further, shape and seal characteristics of the balloons allow for a more even distribution of pressure exerted by the cryogenic fluid. Balloons with outward seals may experience delamination and bursting because all the pressure exerted within the balloon is pushing outward, essentially pulling the balloon away from the medical device. In contrast, the seals of balloons as presented herein are strengthened with increased pressure because the cryogenic fluid, as it is expelled in an outward direction and deflected from the balloon surface within the chamber of the balloon, presses against the inverted necks and reinforces the seals. Although not expressly shown, it will be understood that a configuration may be presented in which the distal necks 98, 100 of the inner 88 and outer 90 balloons may be inverted, whereas both proximal necks 94, 96 may be everted and attached to the device in the manner shown and described in FIGS. 6-9).

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

Referring now to FIG. 10, an exemplary system in accordance with the present invention is shown. The system 10 may be the same as or similar to the system 10 shown and described in FIGS. 1-9, and may generally include a catheter 12 having one or more treatment elements 16, such as one or more balloons, for thermally treating an area of tissue, and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof.

Like the balloon 16 of FIGS. 1A-5, the balloon 16 of FIGS. 10-14 may be coupled to the distal portion 22 of the elongate body 18 of the catheter 12 and in fluid communication with one or more lumens. The balloon 16 may define a proximal opening or neck 80 that is affixed to or coupled to the distal portion 22 of the elongate body 18 with a proximal seal 86, and may further define a distal opening or neck 82 that is affixed to or coupled to the actuation element 24 with a distal seal 84. For example, the actuation element 24 may include a proximal portion (not shown) and a distal portion 25, and may be movably disposed within the elongate body 18, such as within a central or main lumen. The distal portion 25 may include a distal tip 28 that is integrated with or coupled to the distal portion 25 of the actuation element 24. The actuation element 24 may lie along the longitudinal axis 17 of the device 12, and be longitudinally movable within the elongate body 18. In this manner, longitudinal movement of the actuation element 24 will affect the shape of the balloon 16, at least when the balloon 16 is inflated. The proximal portion of the actuation element 24 may be in mechanical communication with one or more steering mechanisms 42 in the handle 18 of the cryotreatment catheter 12, such that the actuation element 24 may be longitudinally extended or retracted using one or more steering mechanisms 42, such as knobs, levers, wheels, pull cords, and the like. Additionally or alternatively, the proximal portion of the actuation element 24 may be in electrical and/or mechanical communication with and operable by the console 16. The device 12 of FIGS. 10-14 may also include a pull wire 54 for steering the distal portion of the device 12. The pull wire 54 may be coupled to the distal portion 25 of the actuation element 24, or it may be coupled to the actuation element 24 at another location. The pull wire 54 may pass over the fluid injection element 31 or between the fluid injection element 31 and the actuation element 24, if the fluid injection element is composed of a semi-rigid material, as shown, for example, in FIG. 11. Further, although not shown, it will be understood that the balloon device 12 of FIGS. 10-14 may include two balloons, similar to that shown and described in FIGS. 1A-9.

In addition to the actuation element 24, the catheter 12 may include one or more lumens. As shown in FIG. 10, the catheter 12 may include, and the balloon 16 may be in fluid communication with, a fluid delivery conduit 30 in fluid communication with a fluid supply reservoir 60, and a fluid recovery lumen in fluid communication with a fluid recovery reservoir 64. Further, the fluid recovery lumen may be in communication with a vacuum 62 to facilitate removal of fluid from the balloon 16 (for example, expanded coolant). One or more fluid injection elements 31 in fluid communication with the fluid delivery conduit 30 may be disposed within the balloon 16. As a non-limiting example, a fluid injection element 31 may include a plurality of windings about the actuation element 24 (as shown in FIG. 10). At least a portion of the fluid injection element 31 may be configured to expand from the actuation element 24 toward the inner walls of the balloon 16 as the balloon 16 is expanded or inflated. As a non-limiting example, the deployment of the fluid injection element 31 may be directly linked to the deployment of the balloon 16 or by a separate mechanism controlled by the console or by the operator via a button, lever, or the like. So, the fluid injection element 31 may be expanded automatically, semi-automatically, or manually independent of the inflation state of the balloon 16.

The one or more treatment elements 16, such as a balloon shown in the figures, may be suitable for energetic or other therapeutic interaction between the catheter 12 and a treatment site. The treatment regions may deliver, for example, radiofrequency energy, cryogenic therapy, or the like to a tissue area in proximity to the treatment region(s). For example, the device 12 may include a first treatment region having a thermal treatment element, such as an expandable membrane or balloon 16 and/or one or more electrodes or other thermally-transmissive components at least partially disposed on the elongate catheter body 18 and/or distal tip 28.

Figure 11:
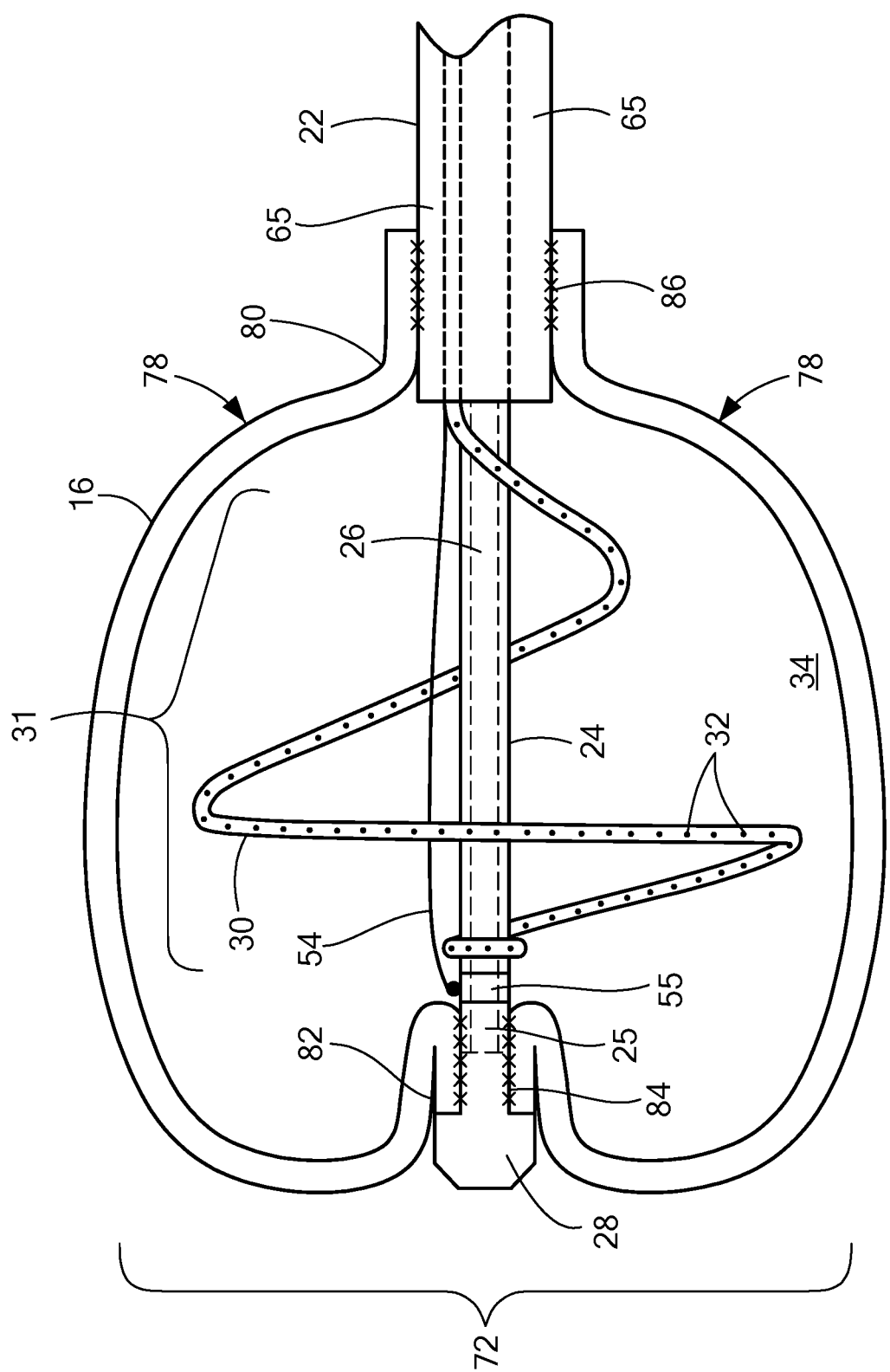
FIG. 11 shows a first non-limiting embodiment of the balloon of FIG. 10, the balloon being in a second configuration.
Figure 12A:
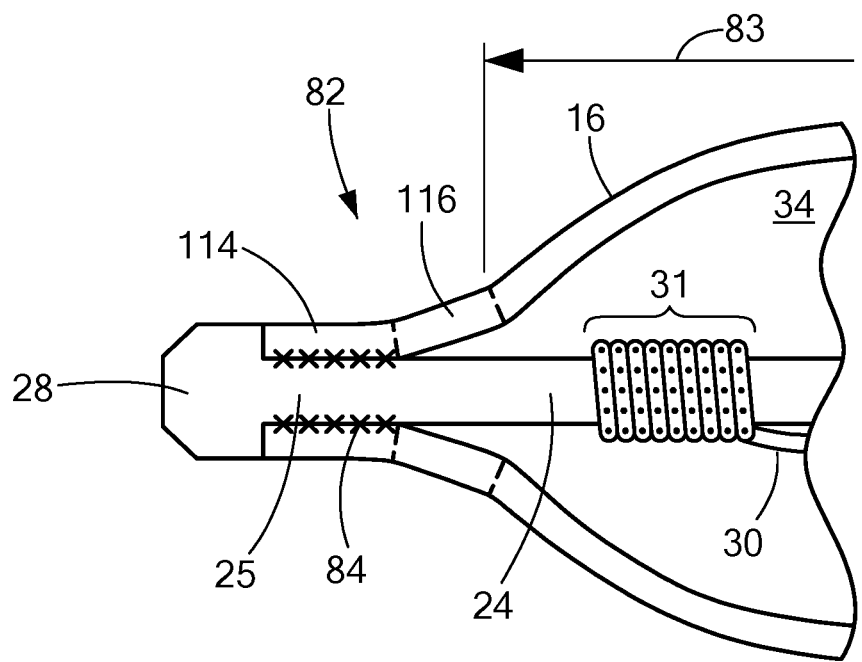
FIGS. 12A and 12B show close-up views of a first exemplary attachment point between a balloon and an actuation element.
Figure 12B:
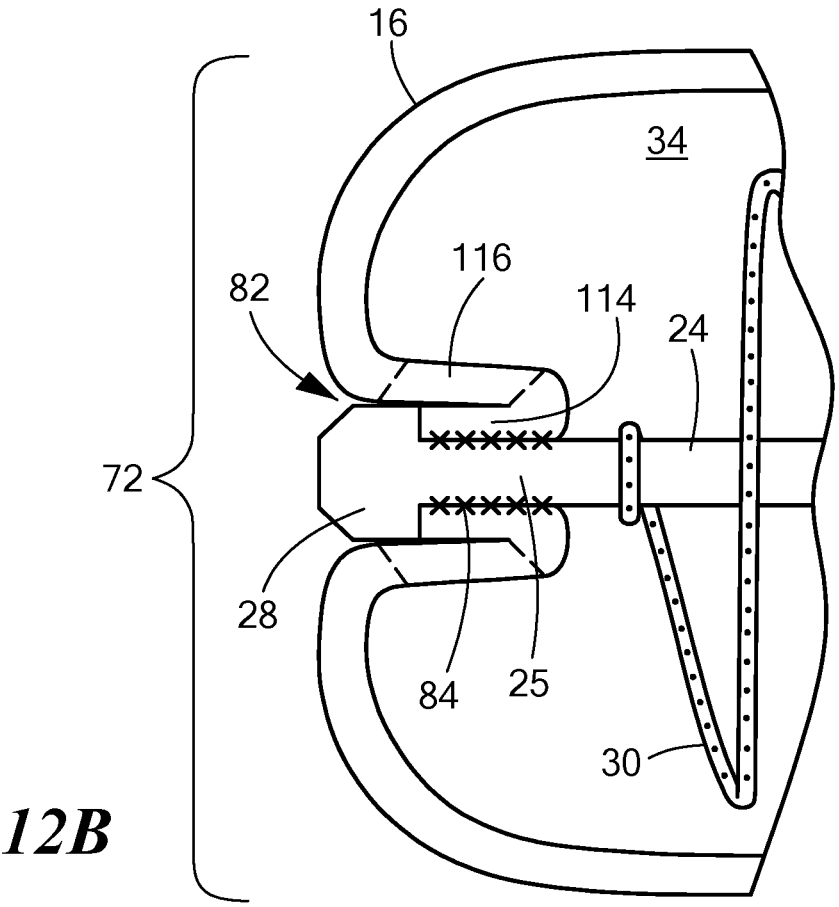
Figure 12C:
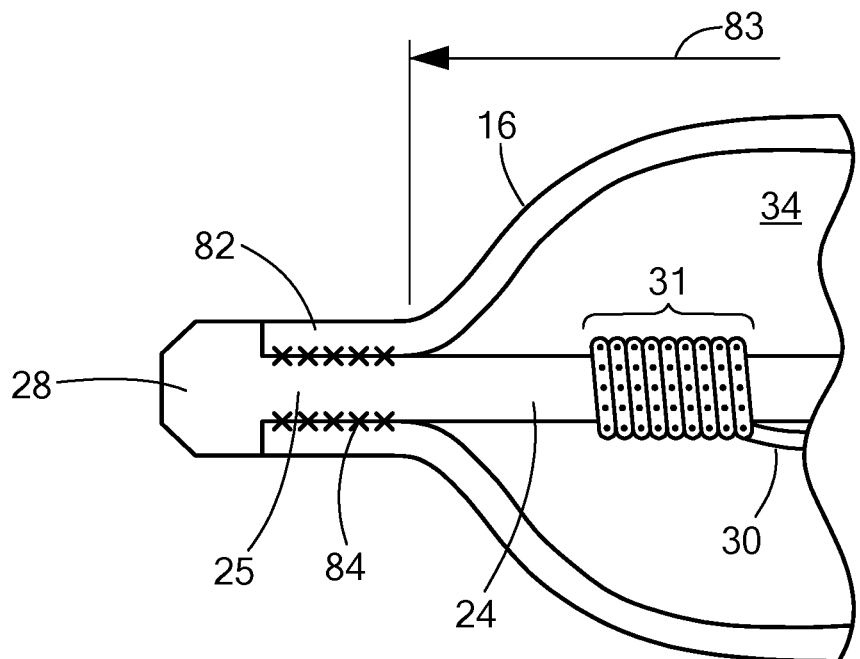
FIGS. 12C and 12D show close-up views of a second exemplary attachment point between a balloon and an actuation element.
Figure 12D:
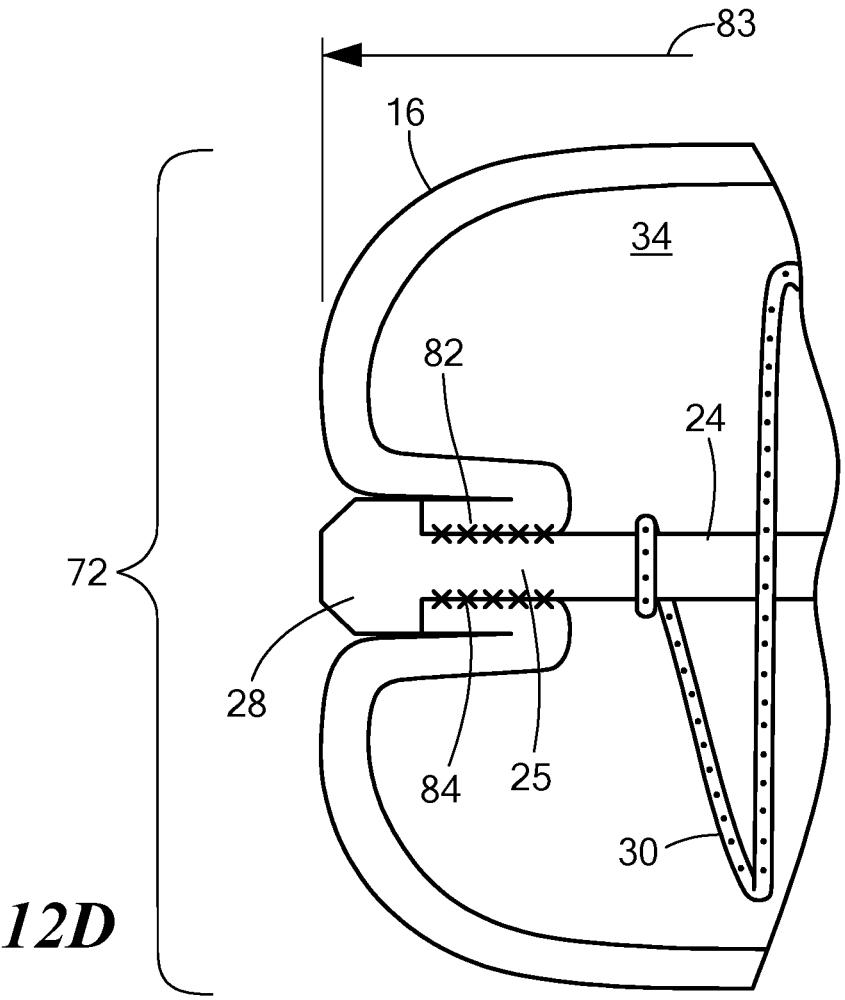
Figure 13:
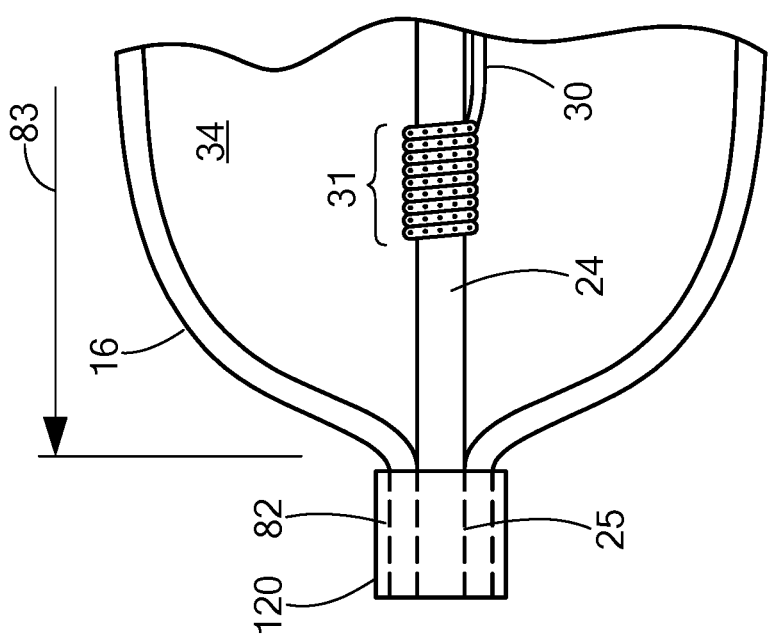
FIG. 13 shows a close-up view of a second non-limiting embodiment of the balloon of FIG. 10, the balloon being in a first configuration.

Referring now to FIGS. 11-13, a non-limiting embodiment of a balloon in a second configuration is shown. As shown in FIG. 10, the balloon 16 may have a first configuration in which the balloon distal neck 82 extends along at least a portion of the distal portion 25 of the actuation element 24, distal to the balloon 16. The balloon may generally have an ellipsoidal or substantially ellipsoidal shape, although the shape may approach a substantially spherical shape, depending on the size of the balloon, the position of the actuation element 24, and/or the material from which the balloon is composed. Further, both the proximal neck 80 and the distal neck 82 may be everted. That is, the proximal and distal necks 80, 82 may each lie outside the interior chamber 82 of the balloon, with the proximal neck 80 extending along at least a portion of the distal portion 22 of the elongate body 18 proximal to the balloon 16 and the distal neck 82 extending along at least a portion of the distal portion 25 of the actuation element 24. In this configuration, the actuation element 24 may be in an extended position or a neutral position.

The actuation element 24 may be slidably and rotatably disposed within the elongate body 18, and may be retractable within the elongate body 18 and extendable distally from the distal portion 22 of the elongate body 18. As such, rotation and/or longitudinal movement of the actuation element 24 may have an effect on the shape of the balloon 16. For example, advancing and retracting the actuation element 24 within the elongate body 18 may act to tension or loosen the balloon, and also may cause the transition of the balloon from the first configuration to the second configuration.

As shown in FIGS. 11 and 13, the balloon 16 in the second configuration may define a distal face 72. The distal face 72 may be formed as a result of the retraction of the actuation element 24 proximally through the elongate body 18 (that is, toward the handle 44 and/or the proximal portion 20 of the elongate body 18), which may cause the balloon distal neck 82 to become inverted. Retraction of the actuation element 24 may also alter the shape of the proximal portion of the balloon 16, and the shape and configuration of the alteration may depend on the balloon material, thickness of the balloon wall in the proximal portion, and/or other factors. As a non-limiting example, the retraction of the actuation element may cause the proximal portion of the balloon to at least partially form a flattened face 78, as shown in FIG. 11. The balloon 16 may be manufactured such that at least a portion of each end of the balloon 16 forms a neck 80, 82, which may have a narrower diameter than the balloon body 83 and/or may have a wall thickness that is different than that of the balloon body 83. For example, wall thickness of the necks 80, 82 may be greater than that of the balloon body 83. Further, an inner surface of a first portion 114 of the balloon distal neck 82 may be attached to the distal portion 25 of the actuation element 24 and a second portion 116 of the balloon distal neck 82 may be free of, that is, not attached to, the actuation element 24. In FIGS. 12A-12D, the attachment (for example, bonding, adhesion, or the like) is generally represented with hash marks. As a non-limiting example shown in FIGS. 12A and 12B, the first portion 114 may be attached to the distal portion 25 of the actuation element 24, such as at a location proximate the distal tip 28. The second portion 116 may be immediately proximal to the first portion 114, between the first portion 114 and the balloon body 83. In the first configuration, at least a portion of an inner surface of the second portion 116 may be in contact with the actuation element 24, or it may be slightly separated from the actuation element 24 (as shown in FIG. 12A). It will be understood that both the proximal and distal necks 80, 82 may be attached to the elongate body 18 and actuation element 24, respectively, by any suitable means, such as being mechanically coupled, or chemically or thermally bonded or adhered to the device.

When the actuation element 24 is retracted, it may draw the balloon distal neck 82 toward the elongate body 18. At a certain distance of retraction that may be referred to as the "transition point," the second portion 116 of the balloon distal neck 82 may separate from the actuation element 24 (or the separation between the distal neck 82 and the actuation element 24 may increase) and the second portion 116 may fold over an outer surface of the first portion 114, and the first portion 114, second portion 116, and at least a portion of the actuation element 24 may lie within the balloon chamber 34 (as shown in FIG. 12B). Alternatively, the inner surface of the entire distal neck 82 may be attached to the actuation element 24 (as shown in FIG. 12C), and retraction of the actuation element 24 may cause the balloon 16 to bend at the junction between the distal neck 82 and the balloon body 83. As shown in FIG. 12D, a portion of the balloon body 83 may be in contact with at least a portion of the outer surface of the distal neck 82.

Figure 14:
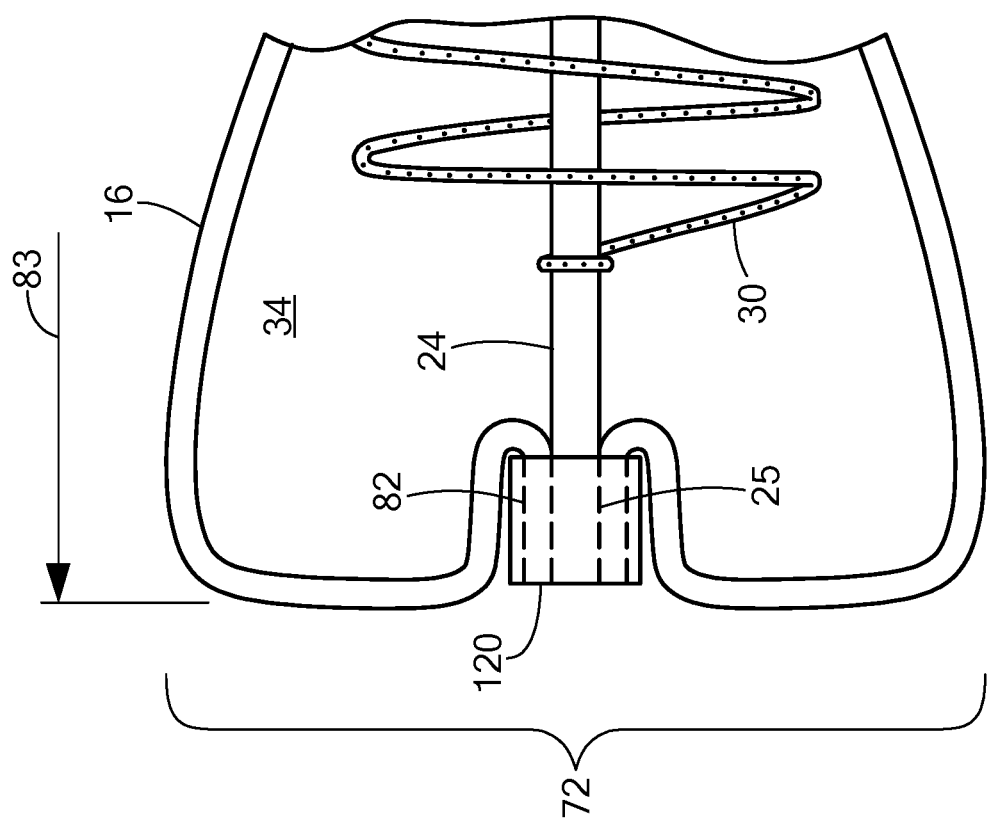
FIG. 14 shows a close-up view of the balloon of FIG. 13, the balloon being in a second configuration.

In the second configuration, the balloon 16 may define a distal face 72; however, depending on the manufactured shape and configuration of the balloon 16, the largest or maximum outer diameter of the balloon 16 may lie at a point that is proximal to the distal face, as shown in FIG. 11. The shape and diameter of the balloon 16 may also depend on the medical procedure for which it will be used. For example, the distal face 72 may define the largest outer diameter if the balloon 16 is used in a procedure that includes a cardiac wall ablation in addition to the pulmonary vein isolation (as shown in FIG. 14). Alternatively, when used for a procedure involving only pulmonary vein isolation, the largest outer diameter may lie at a point that is proximal to the distal face 72. As a non-limiting example, this point may be approximately 6 mm proximal to the distal face 72 for a 28 mm polyurethane balloon. Although the balloon 16 shown in FIG. 13 includes a distal tip and that of FIG. 14 does not, the presence of a distal tip itself may not necessarily affect the shape of the balloon 16 in the second configuration, including the location of the maximum outer diameter. Further, it will be understood that the balloon may have any of a variety of shapes, including conical or pear-shaped.

As is shown in FIG. 13, in one embodiment the first portion 114 of the balloon distal neck 82 may be mechanically coupled to the actuation element 24. For example, the distal tip 28 may be disposed over the first portion 114, thereby locking the first portion 114 in place against the actuation element 24. Instead, the device 12 may not include a distal tip 28. Instead, a collar 120 may be used to mechanically couple at least a portion of the first portion 114 to the actuation element 24. Alternatively, the entire distal neck 82 may be mechanically coupled to the actuation element 24 (as shown in FIG. 13). In either embodiment, use of the collar 120 may provide a device having a shortened distal portion, which may prevent unintended injury or trauma to the patient's anatomy during delivery and/or treatment. Further, the collar 120 may be disposed completely or almost completely within the balloon chamber 34 when the balloon 16 is in the second configuration, without protruding from the balloon distal face 72 (as shown in FIG. 14).

As shown in FIGS. 11, 12B, 12D, 14, and 18, retraction of the actuation element 24 may cause the fluid injection element 31 to expand outward from the actuation element 24 toward the inner walls of the balloon 16. For example, the fluid injection element may have a neutral position in which it is closely coiled or wound about the actuation element, as shown in FIG. 10. This may be referred to as a first or coiled configuration (for example, as shown in FIG. 10). A proximal portion of the fluid delivery conduit 30 may be affixed to a portion of the device 12, such that retraction of the actuation element 24 creates slack in the fluid delivery conduit 30, thereby causing the coils in the fluid injection element 31 to expand away from the actuation element 24, bringing the ports 32 of the fluid injection element 31 closer to or proximate the inner wall of the balloon 16. Alternatively, the fluid injection element 31 may be composed of a shape memory material, such as Nitinol, that has a first, closely wound shape at a first temperature (for example, room temperature or body temperature) and transitions to a second, expanded shape once the material's transformative temperature is reached. For example, the fluid injection element 31 may change shape to that shown in FIG. 11 when coolant begins to circulate within the balloon chamber 34, lowering the fluid injection element 31 to the transformative temperature. This may be referred to as a second or expanded configuration (for example, as shown in FIG. 11). The maximum diameter that may be achieved in the fluid injection element 31 may be defined by the length of the fluid delivery conduit 30, the distance that the actuation element 24 may be retracted, the material from which the fluid delivery conduit 30 is composed, or other factors. However, it will be understood that the fluid injection element 31 may have any of a variety of shapes or configurations that allow it to expand as the balloon expands. That is, the fluid injection element 31 may expand in order to prevent the balloon wall from moving too far from the ports 32. The closer the ports 32 and fluid injection is to the balloon wall, the greater the cooling capacity of the balloon 16. An expandable fluid injection element 31 may affect the distance and angle of one or more apertures in the fluid injection element 31 to deliver coolant toward the balloon inner surface. Additionally, the device 12 may include one or more fluid injection tubes that are likewise transitionable.

It will be understood that the balloon may have any of a myriad of shapes, both in the first configuration and the second configuration. Further, the balloon 16 may include one or more material layers providing for puncture resistance, radiopacity, or the like. Still further, the treatment element may include more than one balloon, such as an inner balloon and an outer balloon, or multiple balloons longitudinally arranged along the elongate body. In such embodiments, each balloon may be in fluid communication with the console 16 independently of the other balloons.

Figure 15:
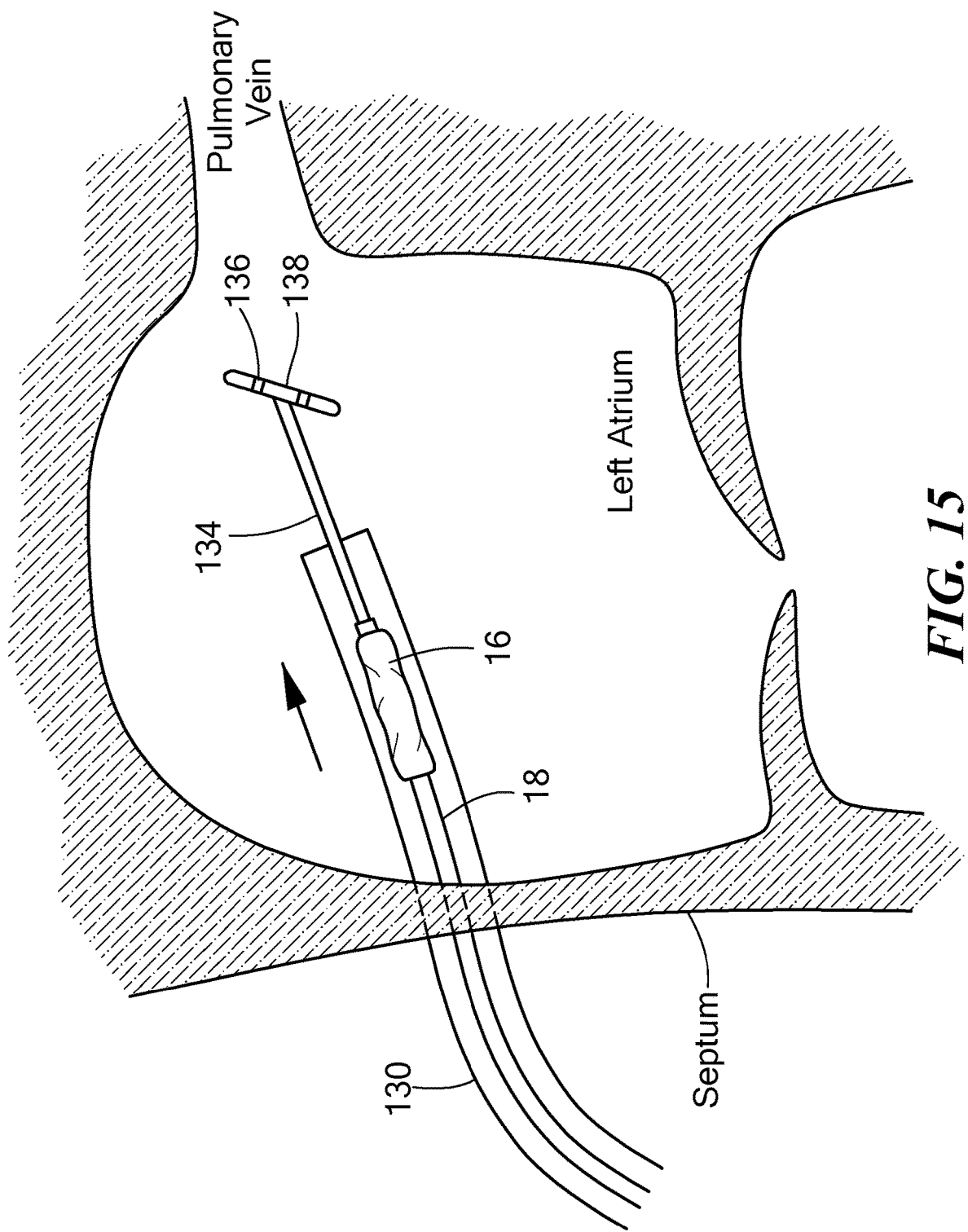
FIGS. 15-18 show a method of positioning a balloon against a pulmonary vein ostium.
Figure 16:
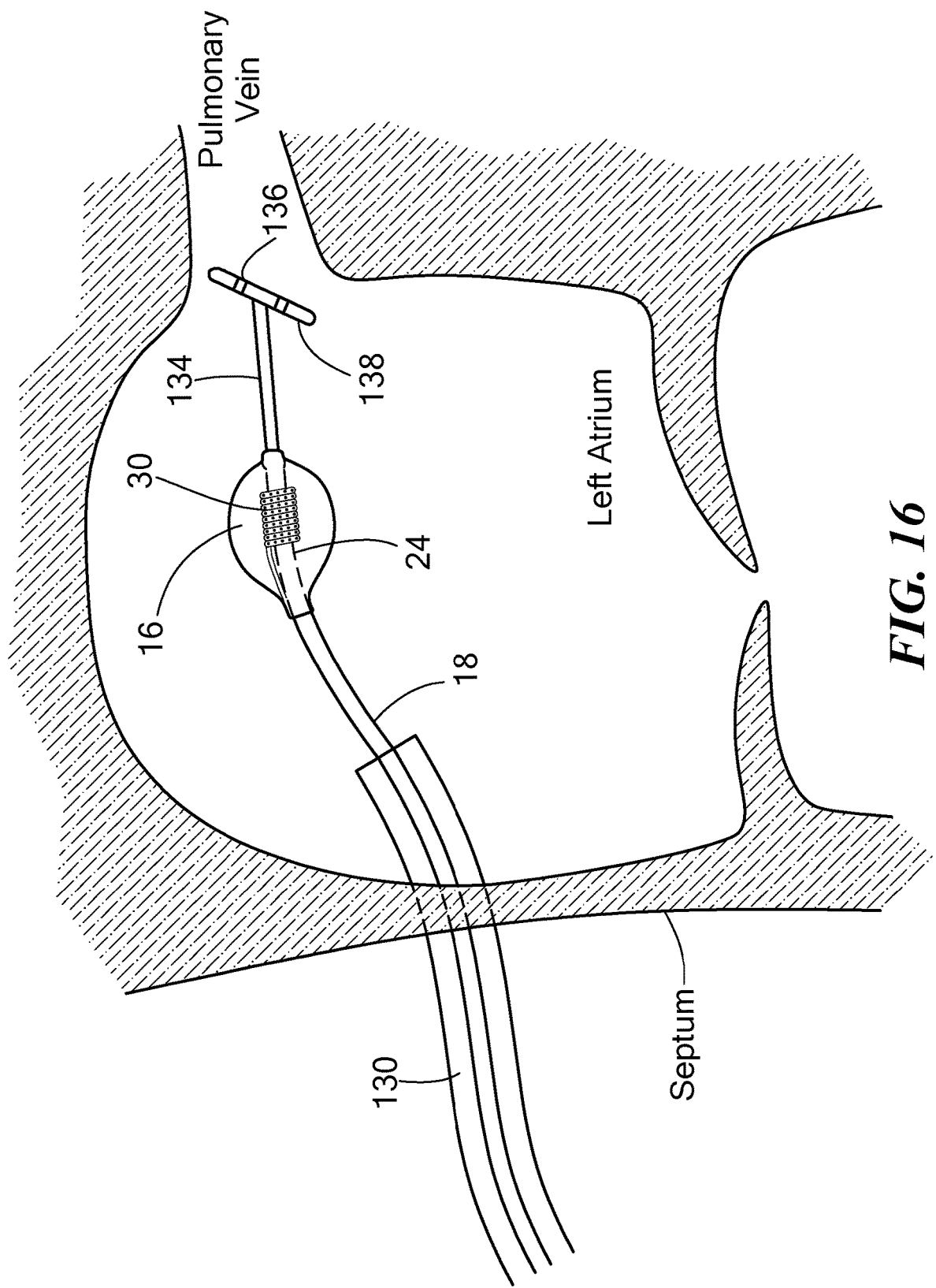

Referring now to FIGS. 15-18, a method of positioning a balloon against a pulmonary vein ostium is shown. The method shown in FIGS. 15-18 may be used for any of the configurations shown and described in FIGS. 1A-14. As shown in FIG. 15 (showing a close-up view of the left atrium of a heart), the catheter 12 may be advanced within a sheath or delivery catheter 130. Further, the actuation element 24 may include a guidewire lumen therethrough, in which case the catheter 12 may be passed over a guidewire or a mapping catheter 134 (as shown in FIG. 16). The mapping catheter 134 may include one or more mapping elements 136, such as electrodes capable of sensing and recording electrograms from cardiac tissue. The one or more mapping elements 136 may be disposed along a distal portion 138 of the mapping catheter 134. Data from the mapping catheter 134 may be employed by the console 16 to adjust console performance, for example, to adjust the duration of coolant into the balloon 16. If a mapping catheter 134 is used, the mapping catheter 134 may be advanced to a target treatment site. For example, the target treatment site may be a pulmonary vein ostium and/or antrum, such as when performing a pulmonary vein isolation. This location may be accessible via a puncture in the septum between the right and left atria, which may be made using the guide wire and/or a puncture device, advanced either in advance of or over the guide wire. However, it will be understood that other means of obtaining access to the pulmonary veins may be used. During delivery, the balloon 16 may be in an uninflated state.

Figure 17:
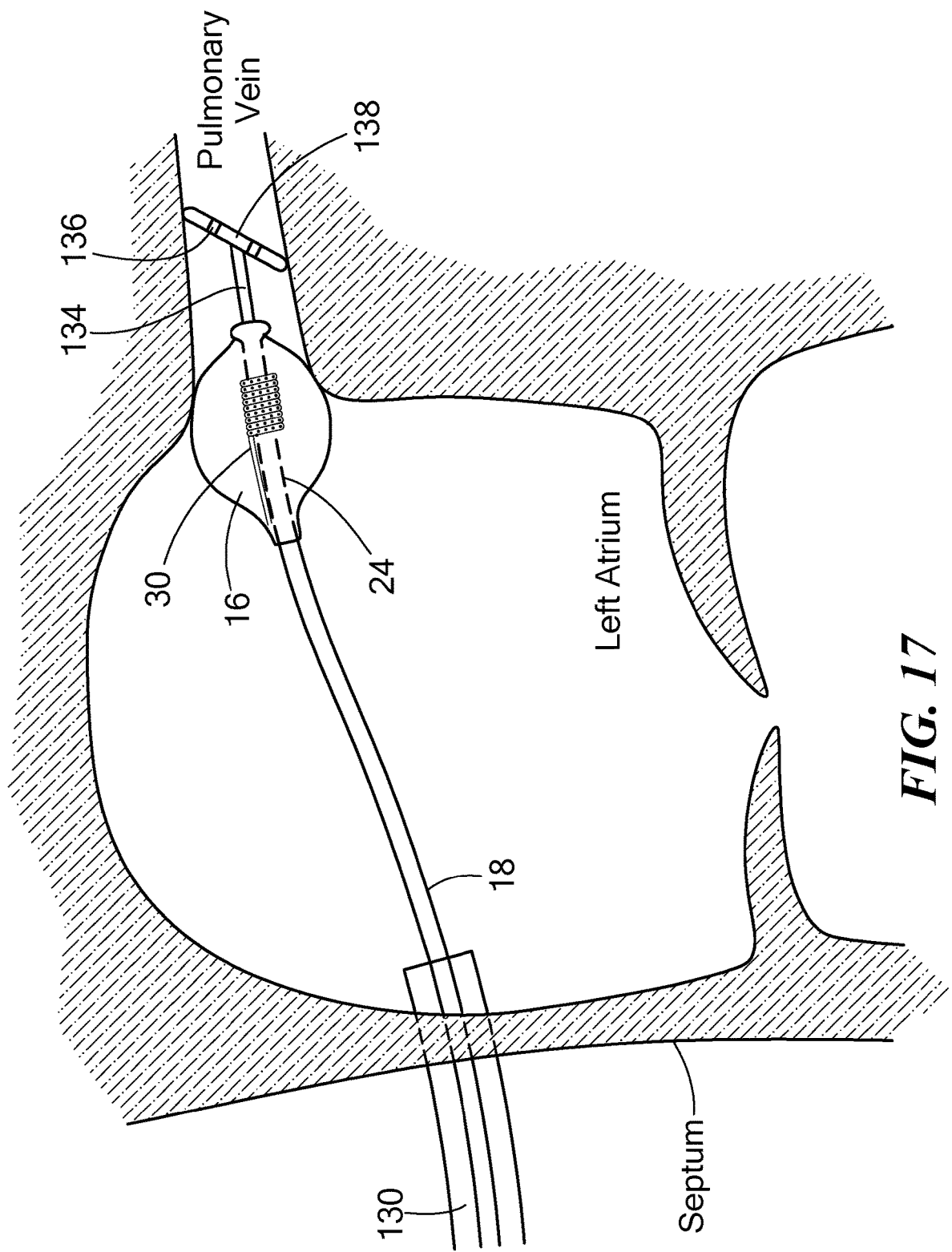

Once the uninflated balloon passes through the catheter 12 and exits the distal portion 22 of the elongate body 18, the balloon 16 may be inflated. This may be accomplished by the circulation of coolant within the balloon chamber 34, although other means of inflation may be used. The inflated balloon 16, in the first configuration, may then be positioned in contact with a pulmonary vein ostium, such that a distal portion of the balloon 16 is located within the pulmonary vein (as shown in FIG. 17). The balloon shape in the first configuration (with an everted balloon distal neck 82) may help the user to locate the pulmonary vein. That is, the shape of the balloon 16 in the first configuration may be easier to position at the pulmonary vein ostium than a blunt-shaped balloon 16, for example, when the balloon 16 is in the second configuration having a distal face 72.

Figure 18:
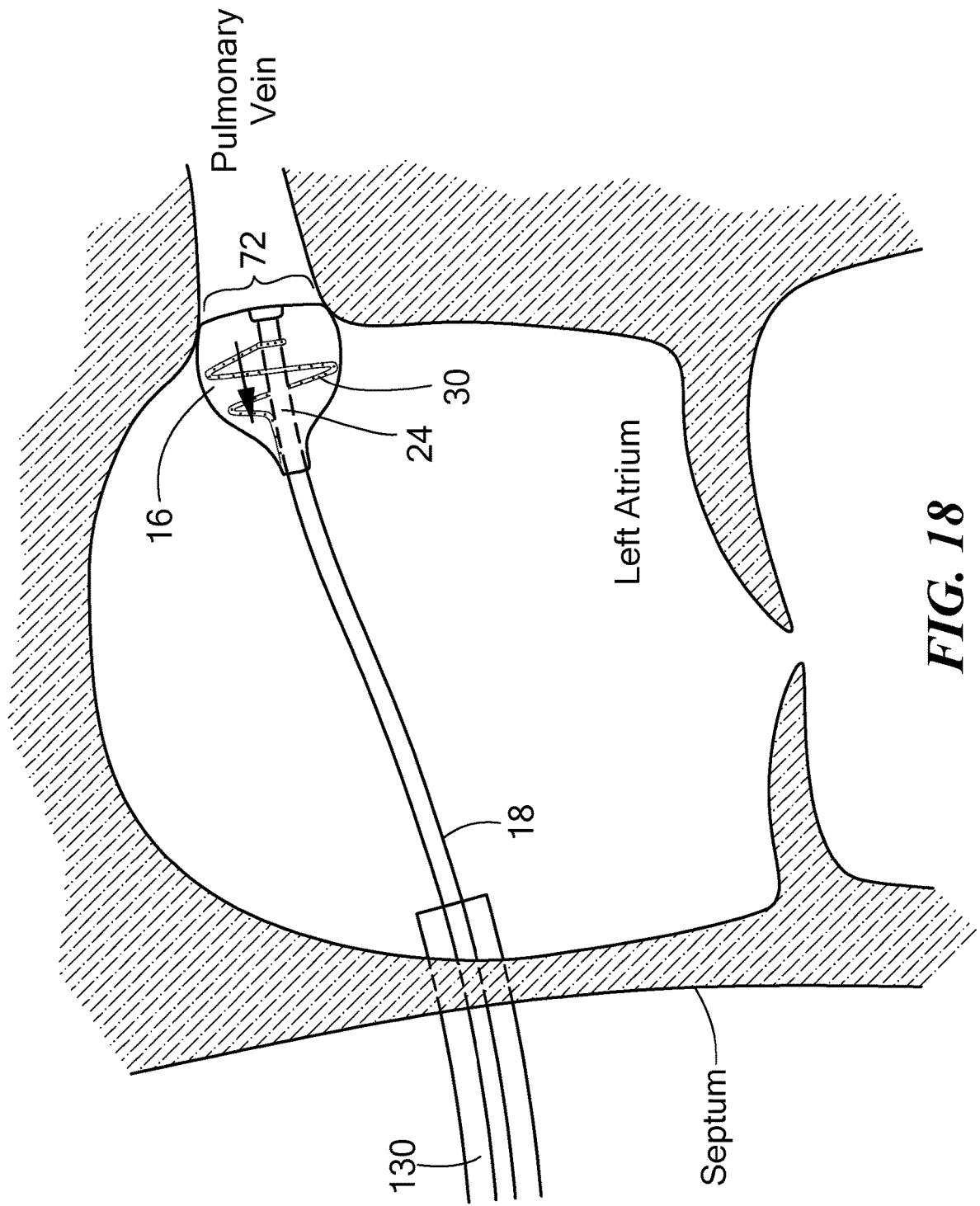

As shown in FIG. 18, the actuation element 24 may be retracted within the elongate body 18 to transition the balloon 16 from the first configuration to the second configuration. The fluid injection element 31 may likewise be transitioned between the coiled configuration (as shown in FIGS. 16 and 17) and the expanded configuration (as shown in FIG. 18). The user and/or the console 16 may effect this transition either once one or more temperature sensors 28 indicate that the balloon 16 has cryoadhered to the tissue, at some predetermined time after the initiation of ablation, or in response to one or more other sensor measurements or system data. For example, one or more sensors (such as pressure or temperature sensors) may communicate data to the one or more processors 58, which may then display or sound an alert to the user or automatically retract the actuation element 24 a predetermined distance in order to transition the balloon 16 to the second configuration. However, it will be understood that the balloon 16 may be transitioned to the second configuration before or in the absence of cryoadhesion. The shape of the second configuration may minimize freezing within the pulmonary vein during cryoablation. Although not shown, the mapping catheter 134 may remain within the pulmonary vein to record mapping data during the ablation procedure, or the mapping catheter 134 may be retracted within the device 12 (as shown in FIG. 15). As discussed in the Background section, freezing tissue deep within the pulmonary vein may increase the risk of complications such as stenosis. The shape of the second configuration, particularly the distal face 72, may also maximize the surface area of the balloon that is in contact with tissue and minimize the surface area of the balloon that is in contact with surrounding blood. Tissue has lower heat transfer characteristics than blood. Therefore, it may be desirable that the balloon 16 be in contact with as much tissue, rather than blood, as possible, in order to prevent heat transfer to the blood. This may maximize heat transfer toward the tissue, thereby decreasing procedure time and dose. That is, the colder the temperature that the balloon can reach and maintain, the shorter the procedure time may be. Not only is this more efficient, but shortened procedure times may also minimize patient injury. Likewise, as discussed above, the fluid injection element 31 may expand or cause to be expanded when the balloon 16 is inflated, also improving the cooling capacity of the balloon 16.

Additionally, the balloon 16 may be maneuvered in the retracted state to other locations in the heart. These locations may be identified anatomically, through sensor feedback from the balloon 16 and/or the catheter 12 (for example, using electrocardiograph (EGM) mapping or using other mapping imaging), or navigation systems external to or incorporated into the system 10 that may be used to identify, for example, likely sources of atrial fibrillation, scar tissue, and/or other areas of disease. The reduction in distal tip length may allow apposition of the balloon 16 body against target tissue in any orientation, including one in which the distal face 72 is in contact with the tissue, while causing little or no mechanical trauma to the tissue. The balloon 16 may also be oriented such that a side surface, the equator, and/or the proximal portion of the balloon 16 are placed in contact with target tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for performing a pulmonary vein isolation procedure, the method comprising:
    positioning a medical device proximate a pulmonary vein ostium, the medical device comprising:
        an elongate body including a distal portion and a proximal portion;
        an actuation element slidably disposed within the elongate body, the actuation element including a distal portion and a proximal portion;
        an inflatable treatment element defining an interior chamber, a first neck, and a second neck, the first neck being coupled to the distal portion of the elongate body and the second neck being coupled to the distal portion of the actuation element, the inflatable treatment element being transitionable between a first configuration and a second configuration, each of the first and second necks being located external to the interior chamber when the inflatable treatment element is in the first configuration; and
        a fluid injection element located within the interior chamber, at least a portion of the fluid injection element being coiled around and substantially in contact with a portion of the actuation element;
    positioning the inflatable treatment element in contact with the pulmonary vein ostium, at least a portion of the second neck being located within a pulmonary vein;
    retracting the actuation element to transition the inflatable treatment element from the first configuration to the second configuration, the second neck being located within the interior chamber when the inflatable treatment element is in the second configuration, retraction of the actuation element causing the fluid injection element to expand away from the actuation element; and
    circulating cryogenic fluid within the interior chamber.

2. The method of claim 1, further comprising initiating a flow of cryogenic fluid within the interior chamber before retracting the actuation element to transition the treatment element from the first configuration to a second configuration.

3. The method of claim 1, further comprising initiating a flow of cryogenic fluid within the interior chamber after retracting the actuation element to transition the inflatable treatment element from the first configuration to a second configuration.

4. The method of claim 1, wherein the inflatable treatment element defines a distal face when the inflatable treatment element is in the second configuration.

5. The method of claim 1, wherein the fluid injection element includes a plurality of ports, at least some of the plurality of ports being proximate an inner wall of the inflatable treatment element when the inflatable treatment element is in the second configuration.

6. The method of claim 1, wherein the second neck of the inflatable treatment element includes a first portion and a second portion.

7. The method of claim 6, wherein the first portion of the second neck is coupled to the actuation element.

8. The method of claim 6, wherein the distal portion of the actuation element includes a distal tip, the first portion of the second neck being coupled to the distal tip of the actuation element.

9. The method of claim 6, wherein retraction of the actuation element causes the second portion of the second neck to separate from the actuation element.

10. The method of claim 6, wherein the first portion and the second portion of the second neck each have an inner surface and an outer surface, retraction of the actuation element causing the inner surface of the second portion of the second neck to be in contact with the outer surface of the first portion of the second neck.

* * * * *